United States Patent [19]

Stevenson et al.

[11] Patent Number: 5,438,086

[45] Date of Patent: * Aug. 1, 1995

[54] HYDROLYTICALLY STABLE PENTAERYTHRITOL DIPHOSPHITES

[76] Inventors: Donald R. Stevenson, 1532 Tremont, Dover, Ohio 44622; Satyanarayana Kodali, 31 Candle Light La., Dover, Ohio 44622

[*] Notice: The portion of the term of this patent subsequent to Nov. 15, 2011 has been disclaimed.

[21] Appl. No.: 232,950

[22] Filed: Apr. 25, 1994

Related U.S. Application Data

[63] Continuation-in-part of Ser. No. 108,658, Aug. 30, 1993, Pat. No. 5,364,895.

[51] Int. Cl.$^6$ .................. C07F 9/6578; C08K 5/527
[52] U.S. Cl. .................................. 524/120; 558/78
[58] Field of Search ........................... 524/120; 558/78

[56] References Cited

U.S. PATENT DOCUMENTS

| | | | |
|---|---|---|---|
| 2,847,443 | 8/1958 | Hechenbleikner | 260/461 |
| 3,192,243 | 6/1965 | Gagliani | 260/461 |
| 3,205,250 | 9/1965 | Hechenbleikner | 260/461 |
| 3,845,142 | 10/1974 | Gurvich | 260/619 |
| 4,064,100 | 12/1977 | Hechenbleikner | 524/120 |
| 4,064,101 | 12/1977 | Mark | 524/120 |
| 4,066,611 | 1/1978 | Axelrod | 524/120 |
| 4,116,926 | 9/1978 | York | 524/120 |
| 4,116,939 | 9/1978 | Cooper et al. | 528/215 |
| 4,187,212 | 2/1980 | Zinke et al. | 524/151 |
| 4,206,111 | 6/1980 | Valdiserri et al. | 520/120 |
| 4,259,534 | 3/1981 | Gurvich et al. | 568/720 |
| 4,261,880 | 4/1981 | Fuji et al. | 224/120 |
| 4,290,976 | 9/1981 | Hechenbleikner et al. | 260/927 |
| 4,299,885 | 11/1981 | Sahajpal et al. | 428/403 |
| 4,305,866 | 12/1981 | York et al. | 524/120 |
| 4,312,818 | 1/1982 | Maul et al. | 260/976 |
| 4,331,585 | 5/1982 | Valdiserri et al. | 524/120 |
| 4,385,145 | 5/1983 | Horn, Jr. | 524/120 |
| 4,403,053 | 9/1983 | Lewis | 524/120 |
| 4,413,078 | 11/1983 | Lewis et al. | 524/120 |
| 4,440,696 | 4/1984 | Maul | 260/976 |
| 4,492,661 | 6/1985 | Maul et al. | 260/976 |
| 4,588,764 | 5/1986 | Lee, Jr. | 524/120 |
| 4,665,211 | 5/1987 | Martin et al. | 558/78 |
| 4,754,077 | 6/1988 | Mina | 568/662 |
| 4,855,345 | 8/1989 | Rosenberger et al. | 524/120 |
| 4,912,198 | 3/1990 | Fontana | 528/370 |
| 4,983,657 | 1/1991 | Humplik et al. | 524/120 |
| 5,137,950 | 8/1992 | Hobbs et al. | 524/120 |

FOREIGN PATENT DOCUMENTS

| | | |
|---|---|---|
| 199997 | 5/1991 | European Pat. Off. . |
| 2156358 | 10/1985 | United Kingdom . |

*Primary Examiner*—Veronica P. Hoke
*Attorney, Agent, or Firm*—Oldham, Oldham & Wilson Co.

[57] ABSTRACT

A class of hydrolytically stable bis(aralkylphenyl)pentaerythritol diphosphites is disclosed, which is suitable as an antioxidant additives in polyolefins, particularly, in polypropylene. The diphosphites are of low volatility, have a high thermal decomposition temperature and resist yellowing when blended into a polyolefin base. A preferred diphosphite is bis(2,4-dicumylphenyl)pentaerythritol diphosphite.

14 Claims, 9 Drawing Sheets

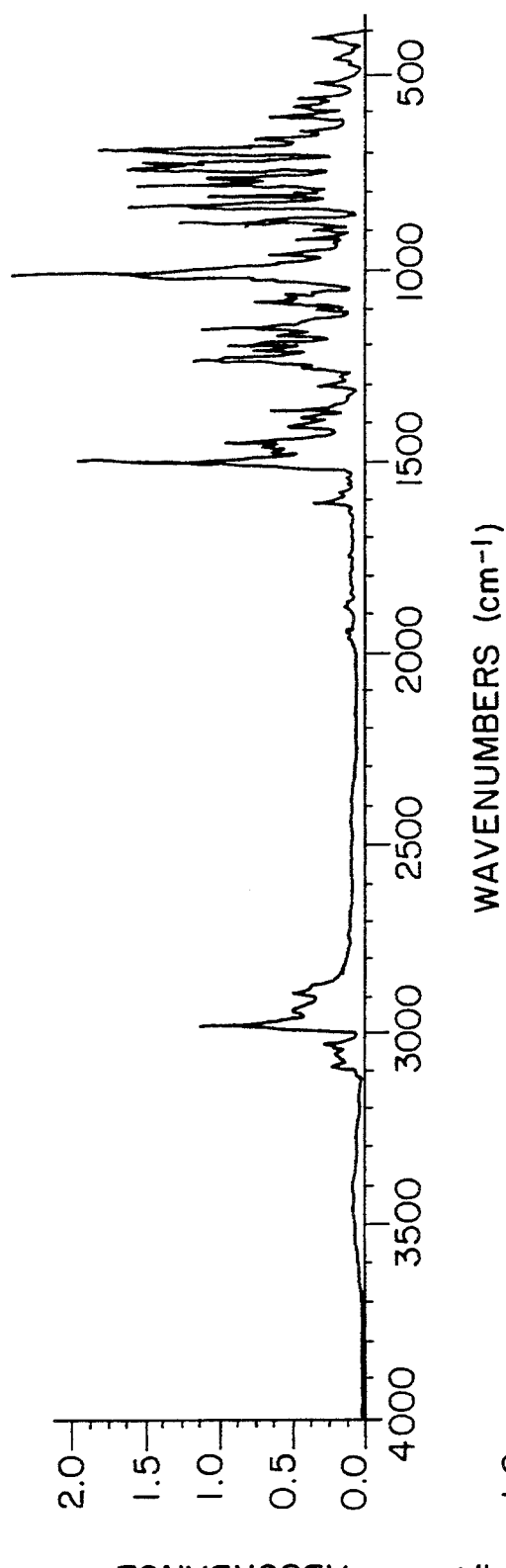
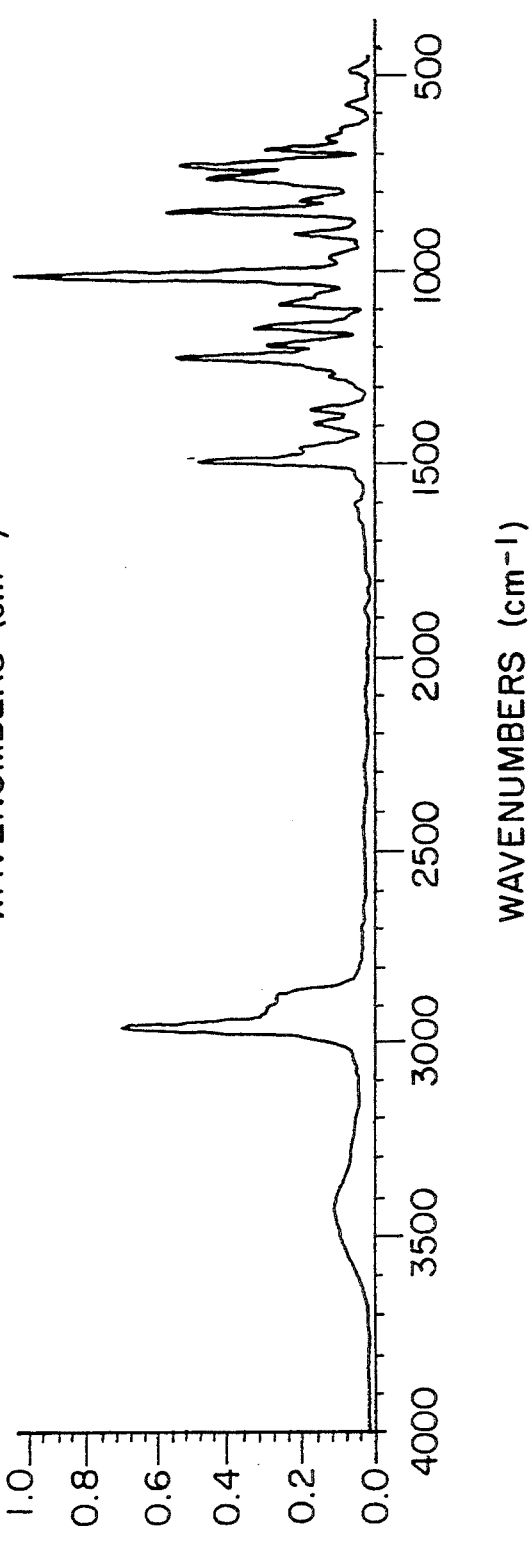
FIG.-9A
FIG.-9B

HYDROLYTICALLY STABLE PENTAERYTHRITOL DIPHOSPHITES

This application is a continuation-in-part of application Ser. No. PCT 93/00499, filed Jan. 20, 1993 and U.S. Ser. No. 08/108,658, filed Aug. 30, 1993, now U.S. Pat. No. 5,364,895.

TECHNICAL FIELD

The invention described herein pertains generally to a new class of phosphites, i.e., a bis(aralkylphenyl)pentaerythritol diphosphites with improved hydrolytic stability, and their ability to be used as a stabilizer for several polymers, e.g., polypropylene, polyesters, polycarbonates, polyamides, polyurethanes, polysulfones, polyimides, polyphenylene ethers, styrenic polymers, acrylic polymers, polyacetals, halide-containing polymers and copolymers therof.

BACKGROUND OF THE INVENTION

Plastics are used in a myriad of widely diverse applications, in automobile parts, in components for houses and buildings, and in packaging from food to electronic parts. Plastics would not be able to perform such diverse functions without the assistance of a very broad range of plastics additives. Without them, some plastics would degrade during processing and, over time, the polymers would lose impact strength, discolor, and become statically charged, to list just a few problems. Additives not only overcome these and other limitations, but also can impart improved performance properties to the final product.

Formulating with plastics additives has always been a tricky business. Incorporating additives into a polymer requires a fine balance between the properties of the polymer and the additive. Formulating a plastic for enhanced ultraviolet light resistance, for example, can have an impact on the polymer's color stability and retention of its functional characteristics. Formulators need to choose additives carefully, so that the additive not only possesses a specific functionality, but that it also minimizes the effect on other additives and the formulated plastic.

Antioxidants are but one class of additives applicable in polyolefin and other polymer resins. These additives retard the oxidative degradation of a plastic. Degradation is initiated when free radicals, (highly reactive species with an unpaired electron), are created in the polymer by heat, ultraviolet radiation, mechanical shear, or metallic impurities. Without the protection of antioxidants, loss of molecular weight, brittleness, discoloration, crosslinking, and deterioration of other polymer properties will occur.

When a free radical is formed, a chain reaction begins that initiates 5polymeric oxidation. Subsequent reaction of the radical with an oxygen molecule yields a peroxy radical, which then reacts with an available hydrogen atom to form an unstable hydroperoxide and another free radical. In the absence of an antioxidant, these reactions become self-propagating, and lead to polymer degradation.

There are two basic types of antioxidants, primary and secondary. Primary antioxidants intercept and stabilize free radicals by donating active hydrogen atoms. Hindered phenols and aromatic amines represent the two main types of primary antioxidants. Secondary antioxidants prevent formation of additional free radicals by decomposing the unstable hydroperoxides into a stable product. Phosphites and thioesters are secondary antioxidants that function by decomposing hydroperoxides, thus preventing free-radical formation. Secondary antioxidants are often used along with primary antioxidants, but can be used alone, especially if they contain a hindered phenolic group within their structure. Together they decrease the discoloration of the polymer and may also regenerate the primary antioxidant.

There are several commercially available phosphites that are used to stabilize polymer materials against color degradation and melt flow degradation. One product which has been found to be especially useful is a bis(2,4-di-t-butylphenyl)pentaerythritol diphosphite as shown by formula (I) described in U.S. Pat. No. 4,305,866 to York, with an initial acid value of ~1.1.

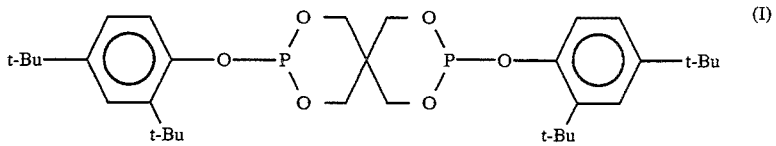

Another product which has been mentioned in the literature is bis(2-t-butyl-4-{α,α'-dimethylbenzyl})pentaerythritol diphosphite as shown by formula (II), described in U.S. Pat. No. 4,983,657 to Humplik.

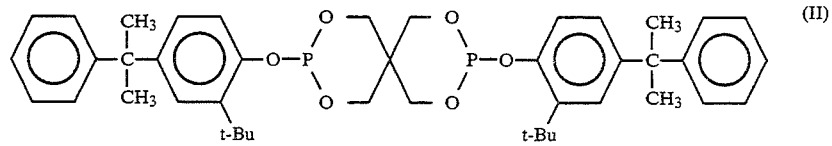

Both phosphites of formulas (I) and (II) have problems in that they are hygroscopic, and therefore, are not hydrolytically stable. On exposure to moisture for a period of time, they have a tendency to lump and become a sticky mass.

Additionally, symmetrical triarylphosphites (e.g., tris-(2,4-di-t-butylphenyl)phosphite) stabilization systems have been described for polyolefins in U.S. Pat. No. 4,187,212 to Zinke et al., as shown for example in formula (III)

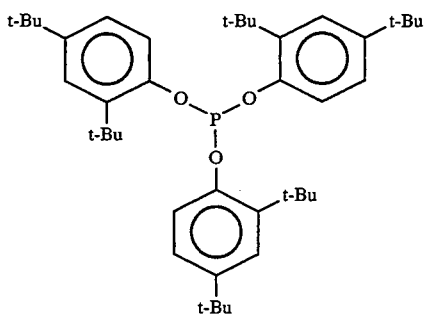
(III)

While this phosphite does possess good hydrolytic stability, it is not as effective as desired for color stability and melt-flow stabilization. Pentaerythritol diphosphites such as shown in formulas (I) and (II) are more effective in maintaining color stability.

Additionally, phosphonites are used as commercial resin additives as shown by generic formula (VI).

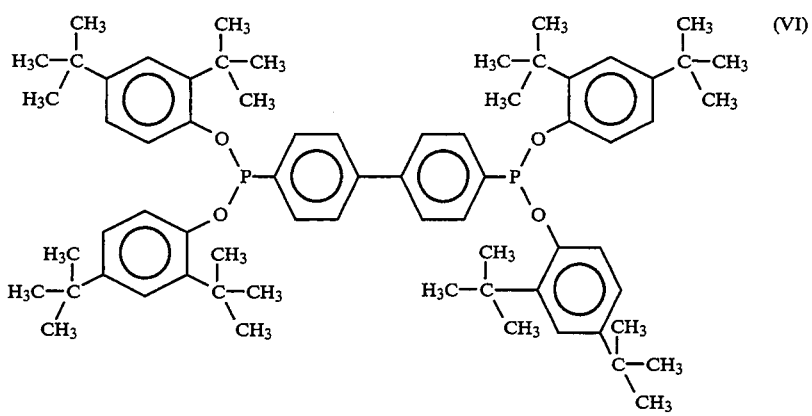
(VI)

While this phosphonite possesses good thermal and hydrolytic stability, its oxidative stability is considered as moderate, consistent with the general observation that the oxidative stability decreases as the number of phosphorus-carbon bonds increases.

To date, there still exists a need to 5provide a phosphite product, based on pentaerythritol, which is slower to absorb moisture, thereby maintaining its effectiveness for longer periods of time in humid conditions.

SUMMARY OF THE INVENTION

In accordance with the present invention, there is provided more hydrolytically stable bis(aralkylphenyl)-pentaerythritol diphosphites, which are suitable as an antioxidant additive in polyolefins, particularly polyethylene and polypropylene, in polycarbonates, polyesters, particularly in polyethylene terephthalate, polyamides, particularly in nylons, polystyrene, impact polystyrene, polyphenylene ether, ABS-type graft copolymers, polyurethanes, polysulfone, polyacrylates and halide-containing polymers.

It is an object of this invention to provide a thermally stable polymer additive of low volatility, which possesses a high thermal decomposition temperature.

It is another object of this invention to provide a polymer additive which is resistant to phosphite hydrolysis upon exposure to moisture for an extended period of time, thereby remaining granular and free-flowing.

It is still another object of this invention to maintain the Hunter yellowness color index number as low as possible thereby indicating that the additive has limited the amount of degradation of the polymer under processing conditions.

It is yet another object of this invention to maintain the melt-flow index of the polymer thereby indicating that the additive has limited the amount of degradation of the polymer under processing conditions.

It is a further object of this invention to provide a method for synthesizing a bis(aralkylphenyl)pentaerythritol diphosphite in improved yield.

It is yet a further object of this invention to demonstrate that a bis(aralkylphenyl)pentaerythritol diphosphite can be used in combination with a class of hindered phenols and U.V. stabilizers to maintain both color and minimize melt-degradation of the polymer in a synergistic manner.

These and other objects of this invention will be evident when viewed in light of the detailed description and appended claims.

DETAILED DESCRIPTION OF THE DRAWINGS

The invention may take physical form in certain parts and arrangements of parts, a preferred embodiment of which will be described in detail in the specification and illustrated in the accompanying drawings which form a part hereof, and wherein:

FIG. 1 is a plot of Yellowness Index as a function of several phosphites in linear low density polyethylene using the following formulations (100 2parts LLPE, 250 ppm CaS+Irganox 1010, and 500 ppm phosphite at 480° F.: (A) base case—no phosphite added; (B) tris-(2,4-di-t-butylphenyl)phosphite (formula III); (C) 2,4-di-t-butylphenyl)pentaerythritol diphosphite (formula I); (D) Sandostab ® PEPQ phosphonate (formula VI); and (E) bis(2,4-dicumylphenyl)pentaerythritol diphosphite (formula V).

FIG. 9A is a Fourier Transform Infra-Red (FTIR) plot of absorbance vs. wavenumbers ($cm^{-1}$) for the diphosphite described as (E) in FIG. 1;

FIG. 9B is a plot of the same information described for FIG. 9A for the diphosphite described as (C) in FIG. 1.

DETAILED DESCRIPTION OF THE INVENTION

Polymer degradation is the deterioration in the physical properties of a polymer caused by chemical reactions involving the backbone of the polymer chain. Symptoms of degradation are yellowing, loss of tensile strength, loss of impact strength, changes in melt-flow, and poor processability. This degradation can be caused by contamination in the polymer, residual catalyst (potentially causing depolymerization), temperature, and light. Degradation tends to occur under the following conditions: polymer drying; polymer pelletizing and compounding; polymer storage and shipment; polymer fabrication processing; and during recycling.

One technique which ameliorates some of the above problems is through the use of an additive, in particular, a phosphite additive. One of the problems with the addition of pentaerythritol phosphite stabilizers has been their tendency to absorb moisture, thereby decreasing the product's ability to flow freely. Another problem has been the experience that at high temperatures (typically greater than 480° F.), some phosphites

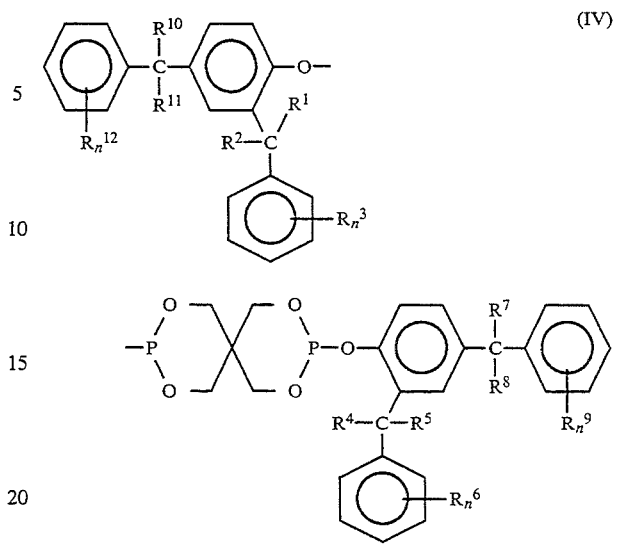

are more hydrolytically stable than prior art pentaerythritol diphosphites, and therefore require less precautions to be taken in their handling, and are more desirable as additives.

Specifically, within the pentaerythritol-based diphosphite of formula (IV), $R^1$, $R^2$, $R^4$, $R^5$, $R^7$, $R^8$, $R^{10}$ and $R^{11}$ are selected independently from the group consisting of hydrogen and alkyl radicals of generic formula $C_mH_{2m+1}$ wherein m ranges from 1 to 4; $R_n^3$, $R_n^6$, $R_n^9$ and $R_n^{12}$ are selected independently from the group consisting of hydrogen, halogens and alkyl radicals of generic formula $C_mH_{2m+1}$ wherein m ranges from 1 to 4, and further wherein n ranges from 0 to 3, and the substituent is located at a position ortho, meta or para to the bridging methylene radical. The halogens are preferably selected from the group consisting of chlorine and bromine and anticipated to impart some additional degree of fire retardancy to the polymer.

In particular, a preferred embodiment of the invention, is a diphosphite in a spiro conformation of formula (V), a bis(2,4-dicumylphenyl)pentaerythritol diphosphite,

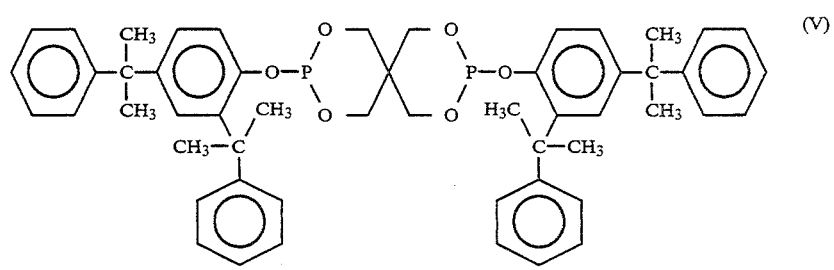

are not particularly effective. It has been found, that pentaerythritol-based diphosphites of the invention, shown in genetic form as formula (IV), although depending upon synthetic methods and conditions employed, a minor amount of the cage conformation, as is shown below in formula (V')

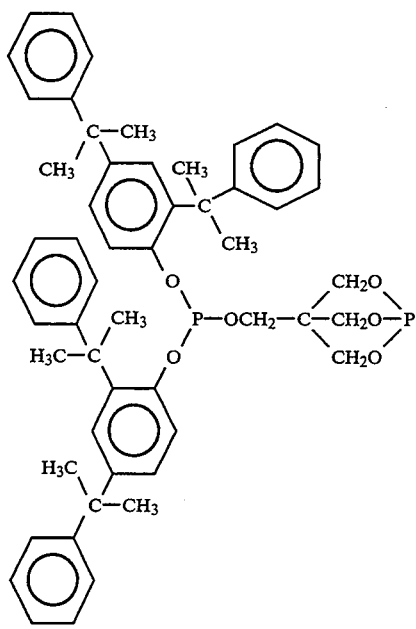

(V')

can be present. Of course, it is possible to include larger amounts of cage conformation in the final product, with the preparation of 10-15% cage conformation possible.

Figure 7A:
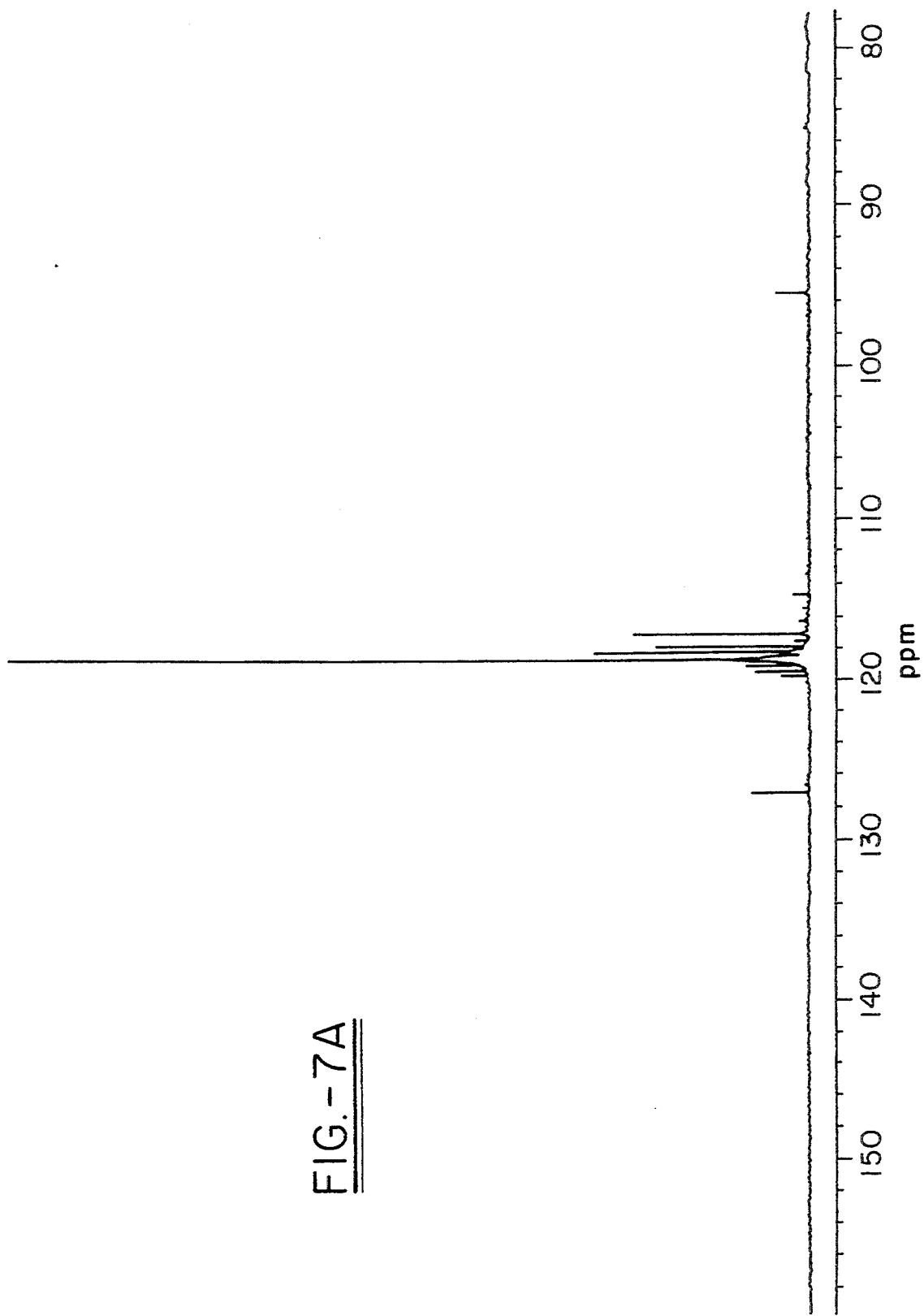
FIG. 7A is a $^{31}P$ NMR spectra of the diphosphite described as (E) in FIG. 1 run in deuterated benzene at 300 MHz.
Figure 7B:
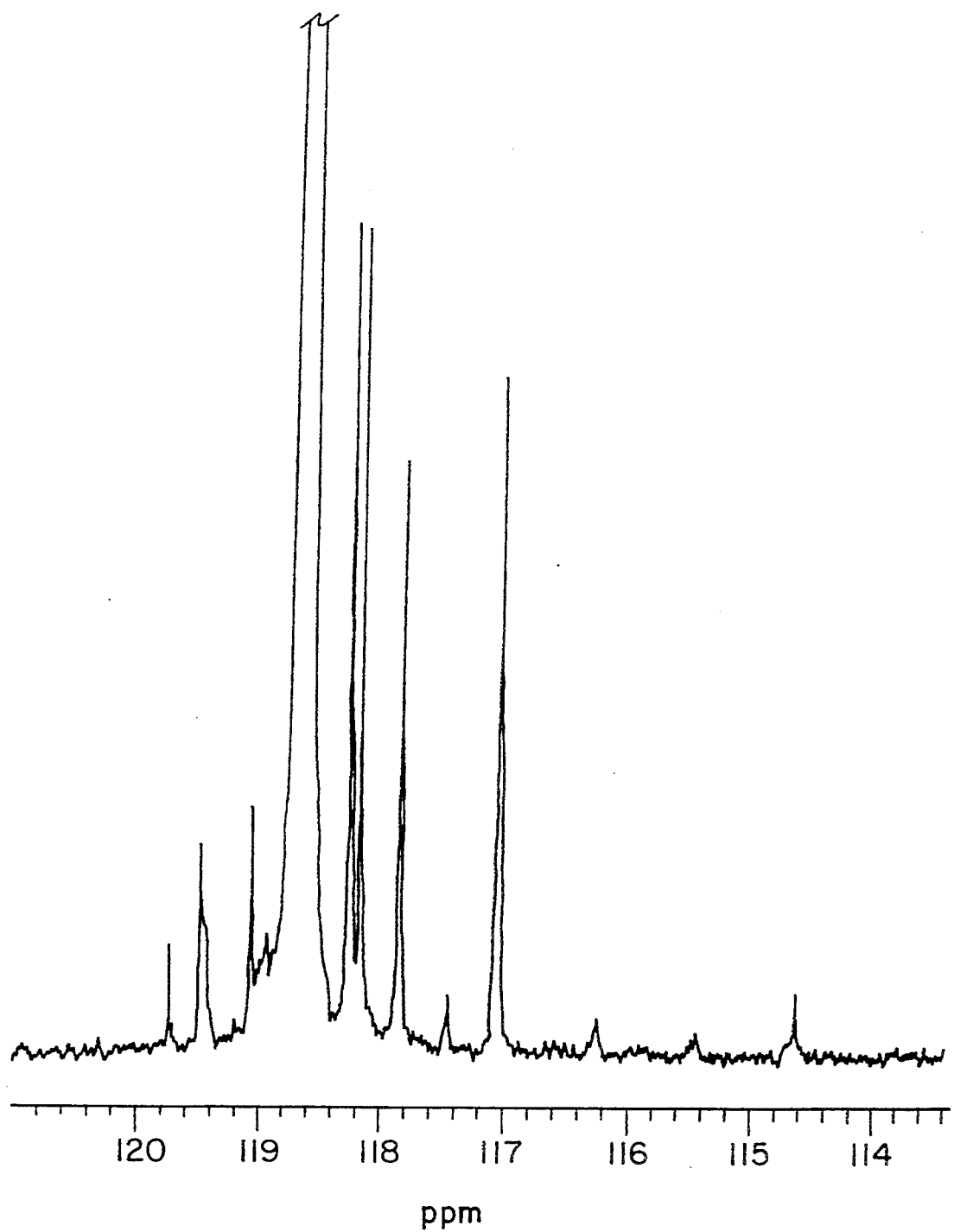
FIG. 7B is an expanded section of the $^{31}P$ NMR spectra shown in FIG. 7.
Figure 8A:
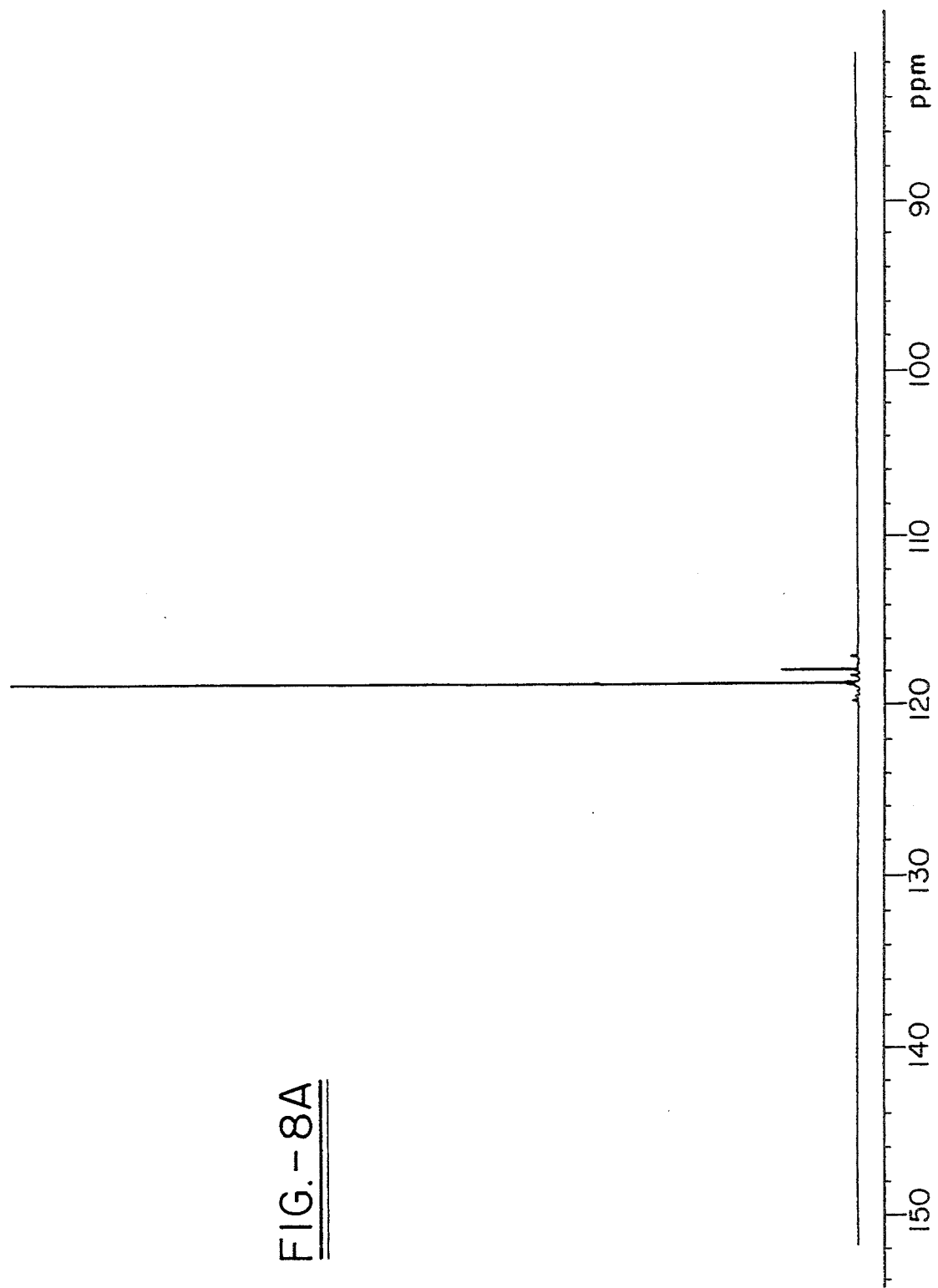
FIG. 8A is a $-P$ NMR spectra of the diphosphite described as (E) in FIG. 1 run in deuterated benzene at 300 MHz.
Figure 8B:
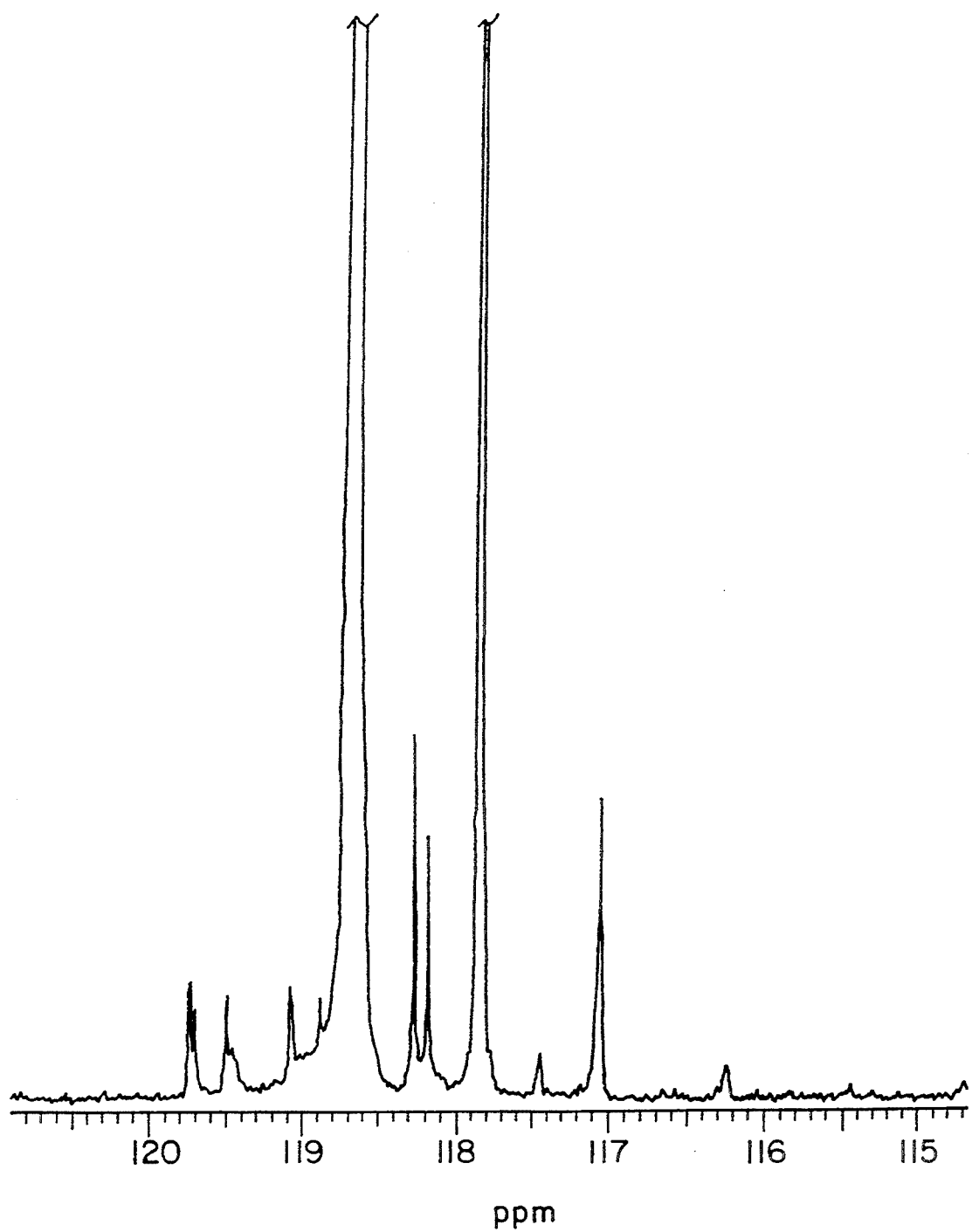
FIG. 8B is an expanded section of the $-P$ NMR spectra shown in FIG. 8.
Figure 9C:
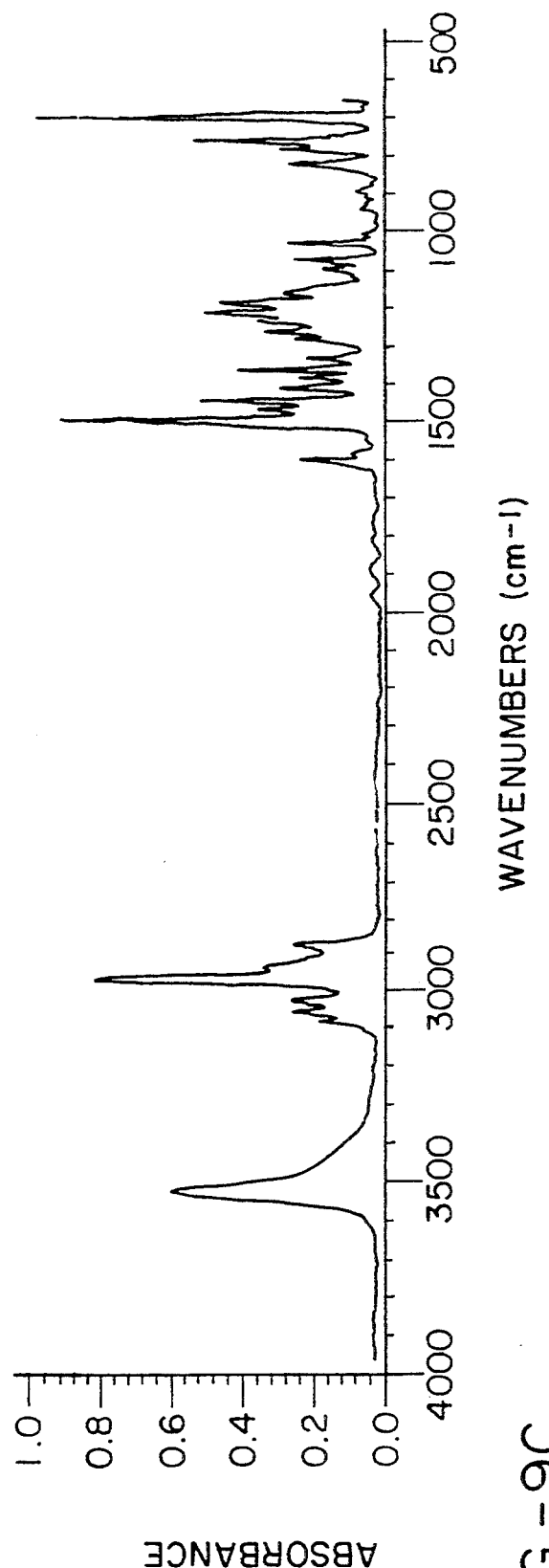
FIG. 9C is a plot of the same information as that previously described for FIGS. 9A and 9B for 2,4-dicumylphenol.

As shown in the 300 MHz $^{31}$P-NMR shown in FIGS. 7-8, wherein the samples were dissolved in deuterated benzene, the ratio can be maximized in favor of the spiro conformation in relationship to the cage conformation. In FIG. 8A, the spiro conformation represents 99.94% while the cage is 0.07%, shown down at 95 ppm on the spectrum. No thiaryl phosphite was detected at all. In FIG. 7A, the spiro conformation represents 99.49% of the sample, whereas the remainder indicated that 0.25% of the sample was of the cage conformation with 0.26% thiaryl phosphite.

By using the synthetic procedures outlined in this application, high purity samples can be obtained. Using differential scanning calorimetry to plot heat flow vs. temperature, a melting point of 232.35° C. was shown, the data of which, when plotted on a Van Hofft plot, indicated the purity to be 99.63%.

Cost and time prohibit real-life testing of stabilizer systems, therefore laboratory tests have been developed to simulate conditions under which degradation occurs. Thermal gravimetric analysis (TGA) is a sensitive technique used to follow the weight change of a sample as a function of temperature, thereby providing information about the thermal stability, volatility and decomposition temperature of the material studied. The test simulates conditions which the polymer would experience during manufacturing and compounding.

As shown in Table I, TGA scans were used to measure the thermal stability of a series of phosphite stabilizers shown previously by formulas (I), (II), (III) and (V). The percentage weight loss of the starting phosphite was determined as a function of temperature.

TABLE I

| | TGA[1] Comparison Temperature at % of Weight Loss | | | |
|---|---|---|---|---|
| | Temp. | | | |
| Percent weight loss | T (°C.) Phosphite (I) | T (°C.) (III) | T (°C.) (V) | T (°C.) (II) |
| 5 | 250 | 258 | 250 | 314 |
| 10 | 275 | 265 | 275 | 332 |
| 20 | 300 | 282 | 300 | 343 |
| 30 | 315 | 293 | 318 | 350 |
| 40 | 320 | 297 | 329 | 354 |
| 50 | 327 | 303 | 336 | 365 |
| 80 | 345 | 318 | 364 | 375 |

[1]DuPont 2000 TGA using a heating rate of 10° C. from room temperature to 800° C. under nitrogen As shown in Table I, the bis(2,4-dicumylphenyl)pentaerythritol diphosphite (V) exhibited good high temperature stability and low volatility in comparison to the bis(2,4-di-t-butylphenyl)pentaerythritol diphosphite of formula (I) and the unsubstituted symmetrical triphenylphosphite, tris-(2,4-di-t-butylphenyl)phosphite) of formula (III) and similar characteristics to the bis(2-t-butyl-4-{α,α'-dimethylbenzyl})pentaerythritol diphosphite of formula (II).

All phosphites will eventually react with water and hydrolyze. As this reaction occurs, an acidic species is produced which is titratable. In the first stage of hydrolysis, the phosphite reacts with a molecule of water to form an alcohol or substituted phenol and dialkyl or dialkylaryl phosphite. The dialkyl or dialkylaryl phosphite once again reacts with water to form a monoester and once more with water to yield the dibasic phosphorous acid. By monitoring a phosphite for the alcohol or phenol and acid content, the extent of hydrolysis can be determined and thereby gauge the product's fitness for use.

The acid number was determined by weighing out a one gram phosphite sample. Approximately 75 ml of methylene chloride was neutralized with 0.02N sodium butylate to a blue-green endpoint using about 4-6 drops of a 0.1% bromothymol blue indicator solution. The neutralized methylene chloride was added to the phosphite sample and dissolved. The solution was immediately titrated with 0.02N sodium butylate to a blue-green endpoint.

A hydrolytic stability comparison was made between the prior art products, formulas (I) and (II) in comparison to new formula (V), by exposing the 5 g samples of the phosphites to 85% relative humidity at about 25° C. for various periods of time, and noting when the powder changed its physical characteristics to either non-powdery or became sticky and lumpy. Without being held to any particular theory, it is proposed that the hydrolytical stability of formula (V) is due to the large bulky groups adjacent to the phosphorus. This provides a good deal of steric hindrance to hydrolysis.

TABLE II

| | Phosphite Hydrolysis[1] | | | |
|---|---|---|---|---|
| | Hours | | | |
| | 0 | 67 | 163 | consistency |
| Phosphite | acid number[2] | | | after 163 hrs |
| (I) | 0.06 | 0.01 | 21.9 | sticky |
| (II) | 0.08 | 0.12 | 10.1 | sticky |
| (V) | 0.67 | 2.36 | 6.13 | granular & |

TABLE II-continued

| Phosphite | Phosphite Hydrolysis[1] | | | |
|---|---|---|---|---|
| | Hours | | | |
| | 0 | 67 | 163 | consistency |
| | acid number[2] | | | after 163 hrs |
| | | | | free flowing |

[1] exposure phosphites to 85% relative humidity at 25° C.
[2] acid number (mg KOH/G) as a function of time (hours)

As can be seen in Table II, diphosphites of formulas (II) and (V) exhibit a lower acid number for longer periods of time, and additionally, for the case of formula (V), the diphosphite remains granular and free-flowing even after exposure to extremely elevated moisture levels for more than 163 hours.

In a more rigorous test, involving exposure of several commercially available diphosphites, i.e., bis(2,4-dicumylphenyl)pentaerythritol diphosphite (formula V) and bis(2-t-butyl-4-{$\alpha,\alpha'$-dimethylbenzyl})pentaerythritol diphosphite (formula II), a trisubstituted symmetrical phosphite, i.e., tris-(2,4-di-t-butylphenyl)-phosphite (formula III) and one diphosphonate, i.e., Sandostab ® PEP-Q, the improved performance of the diphosphite of formula (II) can once again be seen.

TABLE III

| | Hydrolytic Stability at 40° C. and 100% Relative Humidity | | | |
|---|---|---|---|---|
| Phosphorus Additive | (V) | (III) | (II) | (VI) |
| Initial TGA (°C.) 50% weight loss | 412 | 351 | 330 | 384 |
| TGA (°C.) weight loss after hydrolysis | 389 | 275 | 188 | 213 |
| Exposure Time (hours) | 700 | 650 | 50 | 250 |
| Comments | free flowing | caked | slushy | sticky/fused |

The exposure temperature effect can be seen with reference to Table IV, wherein a TGA weight loss comparison after exposure to 100% Relative Humidity at 40° C. is shown at a series of temperatures. The performance of several commercially available diphosphites, i.e., bis(2,4-dicumylphenyl)pentaerythritol diphosphite (formula V) and bis(2-t-butyl- 4-{$\alpha,\alpha'$-dimethylbenzyl})pentaerythritol diphosphite (formula II), a trisubstituted symmetrical phosphite, i.e., tris-(2,4-di-t-butylphenyl)phosphite (formula HI) and one diphosphonate, i.e., Sandostab ® PEP-Q, were once again measured.

TABLE IV

| TGA Comparison Weight Loss after Exposure to 40° C. and 100% Relative Humidity | | | | |
|---|---|---|---|---|
| Phosphorus Additive | (V) | (III) | (II) | (VI) |
| 100° C. | 0.23 | 0.73 | 0.80 | 1.60 |
| 150° C. | 0.54 | 6.20 | 13.50 | 10.80 |
| 200° C. | 1.65 | 10.80 | 55.30 | 42.60 |
| 250° C. | 4.31 | 27.80 | 62.50 | 65.40 |
| 300° C. | 5.68 | 88.60 | 67.90 | 71.80 |
| 350° C. | 9.52 | 95.20 | 70.70 | 75.00 |
| 400° C. | 57.78 | 95.90 | 74.70 | 79.30 |
| Exposure Time (hrs) | 700 | 650 | 50 | 250 |
| Comments | free flowing | caked | slushy | sticky/fused |

Tests which simulate compounding and fabrication include measurements of the polymers' torque rheometry using a Brabender and multiple pass extrusions. These tests subject the molten polymer to heat and shear for extended periods of time. After the test exposure, the polymer is prepared into samples which can be used for physical property, color, and viscosity testing. A Brabender plasticorder PL2000, multipurpose instrument was used to study the viscosity or flow properties of polymer materials under various temperatures and shear rates. For testing, samples were prepared by accurately weighing additives to be added to the polymer (e.g., polypropylene). They were dry blended in a plastic 1000 ml beaker by shaking for approximately 5 minutes.

The Brabender consisted essentially of a measuring head with roller blades, drive control and measuring unit. For the series of tests 5performed, the temperature was set at 200° C. and the speed was 100 rpm. The sample weight was 39 g. The length of the time of the test was approximately 12–40 minutes. The sample to be evaluated was charged to the mixer head by means of a loading chute ram on a 5 kg weight. The Brabender then continuously recorded torque, which is a measure of viscosity at a constant temperature of 200° C. over a time period varying from 0–40 minutes. Torque and temperature were continuously monitored. Torque gives an indication of the viscosity of the polymer. For most polymers, as the polymer degrades, the viscosity decreases and the torque decreases. Immediately upon conclusion of the test, the measuring head was removed. Using a brass knife, a sample was quickly removed to be used for color determination from the mixing head and placed on a clean stainless steel plate. The sample was measured for color determination. When cool, the sample was placed between two polished plates and inserted in a Carver press for 6 minutes at 5 metric tons of pressure and a temperature of about 150° C. After pressing the plates containing the samples, they were cooled for 6 minutes, the sample removed and the color read on a Hunter Colorimeter. The Brabender also computed the specific energy imparted to the sample over the period of time the evaluation was carded out. The higher the specific energy for a given period of time, the less the polymer degraded.

Melt indexes were measured in accordance with the requirements of Condition L of ASTM D 1238. The test method covers measurement of the rate of exudation of molten resin through a die of a specified length and diameter under prescribed conditions of temperature and load. The results of this test give some indication of the molecular weight of the polymer. For polypropylene, as the polymer is degraded and the molecular weight decreases, the melt index or flow through the orifice increases. For Condition L, the temperature is 230° C. with a load of 2.16 kg. Melt index or melt flow is given in numbers of g/10 minutes.

Color measurements were determined using a Hunter Lab D25-PC2 Delta Processor. This processor calculates the yellowness index per ASTM D1925 and ASTM E3 13. The industrial standard for measuring color for polymer such as polyethylene and polypropylene is the yellowness index. Visually, yellowness can be associated with scorching, soiling and general product degradation by light, chemical exposure or processing variables. Yellowness Index, ASTM D1925 is used to measure these types of degradation for plastics and paint industries. The test is carried out by comparing the yellowing of the sample to a white standard. The lower the number YI, the whiter the sample and the less degradation. The higher the YI, the yellower the sample and indicates more degradation.

Typically polymers such as polypropylene, polystyrene, polyethylene terephthalates (PET), polyalklylene terephthalates, and polycarbonates will tend to break down or chain scission as they are processed at higher temperatures for a period of time. This will result in an increase in melt index. Polyethylene on the other hand, can increase in molecular weight due to crosslinking and oxidation. When evaluating polyethylene by melt index, and basically for all polymers, it is desirable that the melt index not change from the beginning to the end.

In regard to the yellowness index, the more the polymer is processed, the higher the yellowness index or the darker the material becomes. Again, it is desirable that there be minimal change in this index during processing.

equally effectively to that of a known state-of-the-art products, formulas (I) and (HI), and significantly better than formula (IID) in discoloration.

The improvement resides therefore, in the ability to outperform phosphites, such as formula (I) and (II) in its resistance to hydrolysis, as indicated in Table (II) and additionally, in its inherent thermal stability as indicated in Table (I).

A multi-extrusion study was performed using phosphite (V), a bis-2,4-dicumylpentaerythritol diphosphite, with several other phosphites using polypropylene in accordance with the amounts shown in Table IV. The samples were blended and extruded at 210° C. through a twin-screw extruder. The extruded material was pelletized and a small sample was retained for melt-flow and color resting. The remaining pellets were extruded

TABLE V

Evaluation of Phosphites in Polypropylene

| Polymer composition | Torque[3] (m-grams) | | | Hunter YI yellowness color index |
|---|---|---|---|---|
| | 12 min | 24 min | 36 min | |
| base[1] | 875 | 550 | 375 | 40.8 |
| base + (I)[2] | 1075 | 720 | 395 | 17.5 |
| base + (II)[2] | 1025 | 700 | 375 | 17.6 |
| base + (V)[2] | 1075 | 725 | 375 | 15.5 |
| base + (III)[2] | 1000 | 685 | 375 | 44.3 |

(1) base formulation
  (a) 100 parts polypropylene, Profax TM 6501 produced by Himont, an isotactic homopolymer with a melt-index of 4, a density of 0.9 g/cm³, a tensile strength of 5,000 psi, and elongation at yield of 12%.
  (b) 0.10 parts Irganox 1076 (octadecyl 3-(3',5'-di-t-butyl-4'-hydroxyphenyl)propionate), formula (VII)

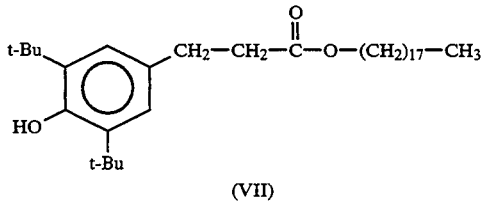

(VII)

(2) 0.2% phosphites added to the base
(3) Brabender temperature 200° C. - 100 rpm As shown in Table III, without the addition of any phosphite additive, the torque, which is a measure of the polymer degradation, measured at 12 min. was significantly lower than the torque measured for samples to which 0.2% phosphites had been added. Additionally, the unstabilized polypropylene exhibited significant discoloration as indicated by the high yellowish color index number. The diphosphite (V) performed again, up to a total of five extrusions.

TABLE VI

Multi-Pass Extrusion Study

| base[1] polymer | Additives | | | melt flow[4] 1st pass | melt flow[4] 5th pass | YI[5] 1st pass | YI[5] 5th pass |
|---|---|---|---|---|---|---|---|
| | Ca[2] | phenol[3] | phosphite | | | | |
| #1 PP | 0.05% | 0% | 0% | 26.9 | 208.3 | 4.6 | 6.7 |
| #2 PP | | 0.1% | 0% | 7.0 | 12.2 | 4.5 | 6.3 |
| #3 PP | | 0.1% | (V) 0.05% | 5.9 | 7.8 | 4.5 | 5.4 |
| #4 PP | | 0.1% | (I) 0.05% | 3.9 | 4.8 | 4.0 | 6.1 |
| #5 PP | | 0.1% | (II) 0.05% | 3.5 | 4.8 | 4.0 | 6.1 |
| #6 PP | | 0.1% | (III) 0.05% | 6.0 | 54.6 | 4.3 | 5.4 |
| #7 PP | | 0.1% | (V) 0.05% | 4.0 | 5.1 | 4.0 | 4.6 |
| #8 PP | | 0.05% | (V) 0.10% | 3.9 | 15.0 | 4.1 | 4.4 |

[1] polypropylene (PP)
[2] calcium stearate
[3] hindered phenol (I-1076 of formula (VII))
[4] melt flow (grams/10 minutes)
[5] Hunter Yellowness Color Index The data clearly shows that the phosphite of formula (V) does improve the stability over the base polymer. The amount of phosphite added is well-known by those skilled in the art, but in general is guided by cost considerations and FDA approval. Typical amounts added however, will generally range from 0.01% to about 0.5%.

While only one hindered phenol is shown in Table IV, there are many different phenolic compounds which are equally suitable for use in the invention, and well-known to those skilled in the art. A non-inclusive list of examples of such suitable phenolic-based compounds would be: Bisphenol TM A (Dow Chemical Co., 4,4'-isopropylidene-diphenol); TEN OX# BHA (Eastman Chemical, butylated hydroxyanisole); ETHANOX TM 330 (Ethyl Corp., 1,3,5-trimethyl-2,4,6-tris(3,5-di-di-t-butyl-4-hydroxybenzyl)benzene); ETHANOX TM 702 (Ethyl Corp., 4,4'-methylene-bis(2,6-di-t-butylphenol)); MIXXIM# AO-30 (Fairmount Chemical Co., 1,1,3-tris(2-methyl-4-hydroxy-5-t-butylphenyl)butane); ANULLEX# BHEB, (Hodgson Chemicals Ltd., 2,6-di-t-butyl-4-ethylphenol); HOSTANOX TM 03 (Hoechst Celanese Corp., bis-[3,3-bis-(4'-hydroxy-3'-t-butyl-phenylbutanoic acid]-glycol ester)); TOPANOL# CA (ICI Americas Inc., 1,1,3-tris(2-methyl-4-hydroxy-5-t-butyl-phenyl)butane); SANTONOX TM (Monsanto Co., 4,4'-thio-bis(6-t-butyl-m-cresol)); SANTONOX# (Monsanto Co., 4,4'-thio-bis(2-t-butyl-m-cresol)); SANTOWHITE TM (Monsanto Co., 4,4'-butylidene-bis(2-t-butyl-m-cresol)); SUSTANE TM BHT (UOP Biological & Food Products, 2,6-di-t-butyl-p-cresol); VANOX TM 1320 (R. T. Vanderbilt Co., Inc., 2,6-di-t-butyl-4-sec-butylphenol); CYANOX# 425 (American Cyanamid Co., 2,2'-methylene-bis(4-ethyl-6-t-butylphenol)); CYANOX# 1790 (American Cyanamid Co., 1,3,5-(4-t-butyl-3-hydroxy-2,6-dimethylbenzyl)-1,3,5-triazine-2,4,6-(1H,3H,5G)-trione); CYANOX TM 2246 (American Cyanamid Co., 2,2'-methylene-bis(4-methyl-6-t-butylphenol)); IRGANOX# 245 (Ciba-Geigy Corp., 1,6-hexamethylene-bis(3,5-di-t-butyl-4-hydroxyhydrocinnamate)); IRGANOX# 1010 (Ciba-Geigy Corp., tetrakis ( methylene-3-(3,5-di-t-butyl-4-hydroxyphenyl)propionate ) methane); IRGANOX TM 1076 (Ciba-Geigy Corp., octadecyl-3-(3'5'-di-t-butyl-4 '-hydroxyphenyl)-propionate); IRGANOX# 3114 (Ciba-Geigy Corp., 1,3,5-tris(3,5-di-t-butyl-4hydroxybenzyl)isocyanurate); and IRGANOX# 3 125 (Ciba-Giegy Corp., 3,5-di-t-butyl-4hydroxyhydrocinnamic acid triester with 1,3,5-tris(2-hydroxyethyl)-s-triazine-2,4,6-(1H,3 H,S H)trione).

Figure 1:
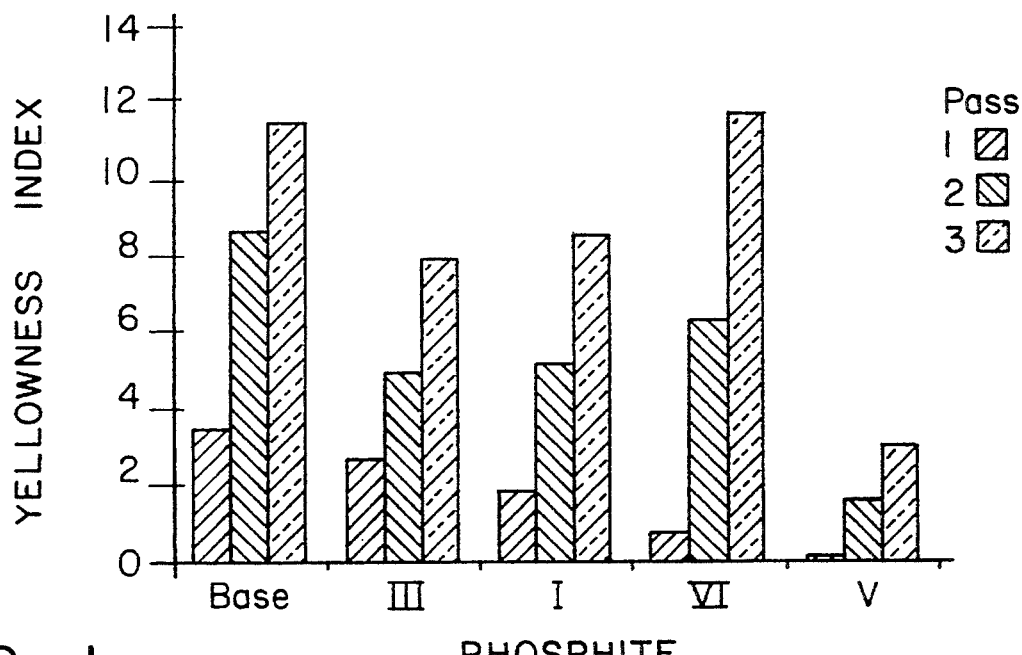
Figure 2:
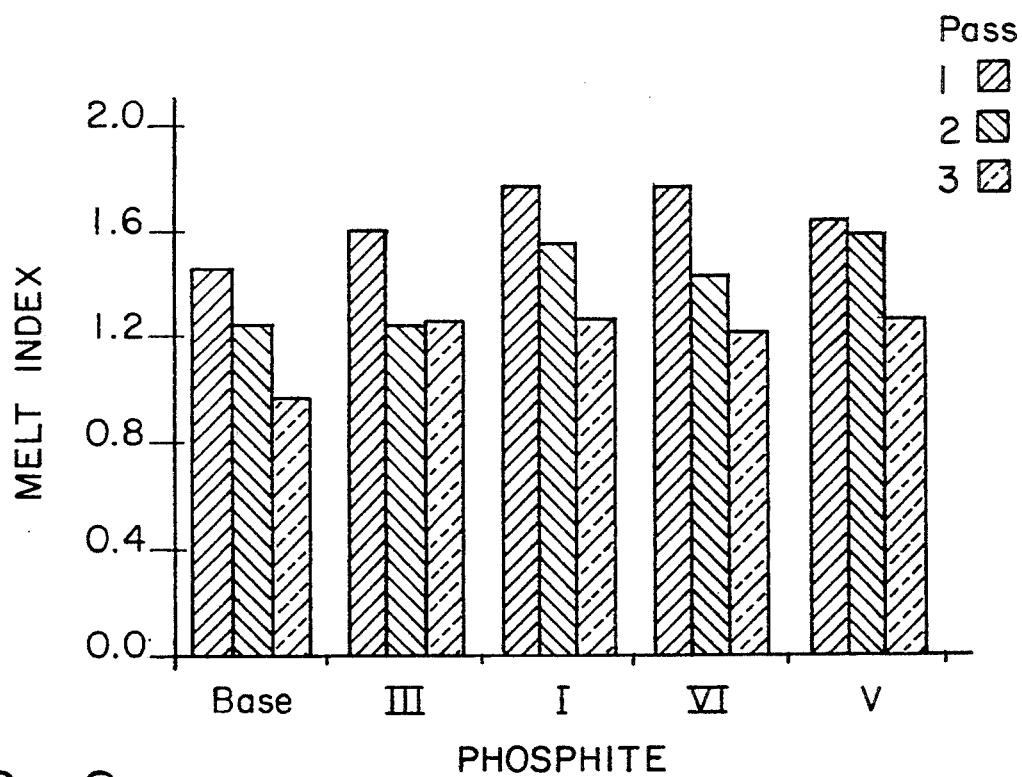
FIG. 2 is a plot of Melt Index vs. the phosphorus-based additives described previously for FIG. 1.

The information presented in FIGS. 1 and 2 represents similar data to that described previously for polypropylene in Table VI above, with the substitution of linear low density polyethylene for polypropylene. The bis(2,4-dicumylphenyl)pentaerythritol diphosphite of formula (V), with a significant degree of aromaticity, was clearly shown to be superior to several commercially available additives, such as that of bis(2-t-butyl-4-{α,α'-dimethylbenzyl})pentaerythritol diphosphite (formula II) wherein an aliphatic substituent is positioned ortho to the diphosphite oxygen and an aralkyl substituent is positioned para to the same oxygen attachment point on the benzene ring, to bis(2,4-di-t-butylphenyl)pentaerythritol diphosphite (formula I) wherein an aliphatic substituent is positioned both ortho and para to the diphosphite oxygen attachment to the benzene ring, and the phosphonite formula (VI) wherein an alkyl substituent is positioned both ortho and para to the phosphorus attachment to the benzene ring.

Figure 3:
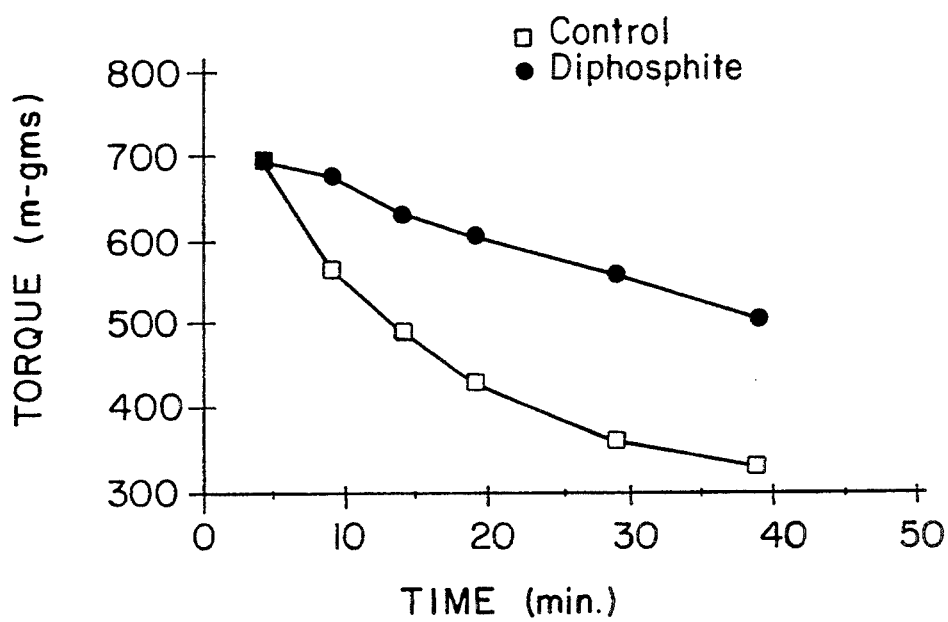
FIG. 3 is a plot of Torque (meter grams) vs. time (minutes) of the addition of 0.2% of the diphosphite described as (E) in FIG. 1 to polybutylene terephthalate (PBT) in comparison to a control sample with no diphosphite added.

FIG. 3 shows the evaluation of the bis(2,4-dicumylphenyl)pentaerythritol diphosphite of formula (V) in polybutylene terephthalate (PBT), a semi-crystalline thermoplastic polyester that can be used in a wide variety of high performance applications, which include both interior and exterior automotive parts including electronic components, industrial manufacturing parts, and household appliance handles and housings. Approximately 0.2% of the diphosphite of formula (V) was added to Ultradur ® B4500 HF PBT, commercially available from BASF, and the Torque Rheometer data displayed wherein the test was run for 40 minutes at 240° C. and 100 rpm.

Figure 4:
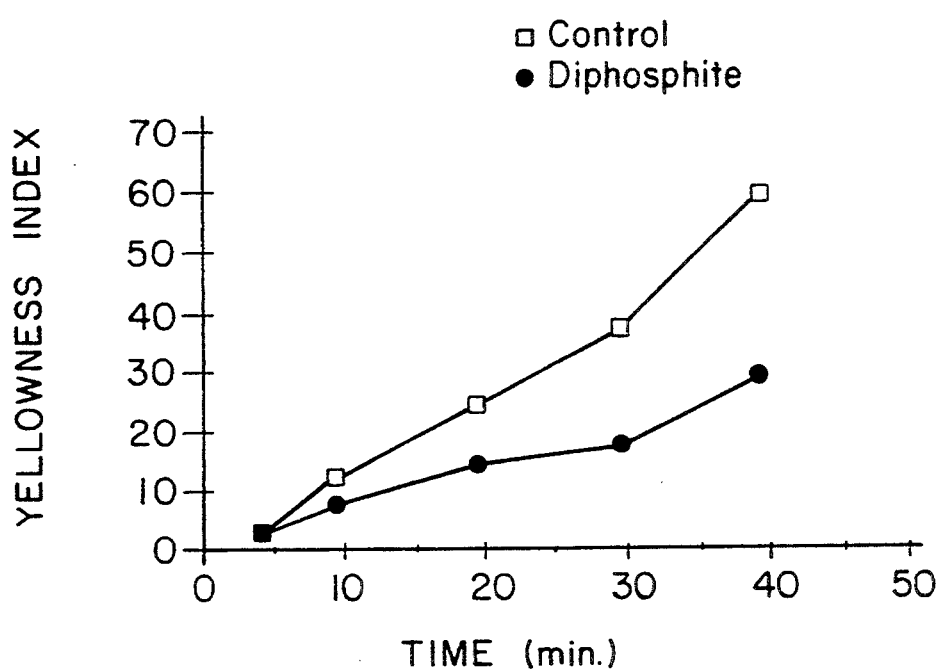
FIG. 4 is a plot of Yellowness Index vs. time (minutes) using the same comparatives shown for FIG. 3.

The color stability of PBT was also improved with the addition of the diphosphite additive as shown in FIG. 4, wherein the Yellowness Index was also measured on samples taken from the Torque Rheometer run above.

Figure 5:
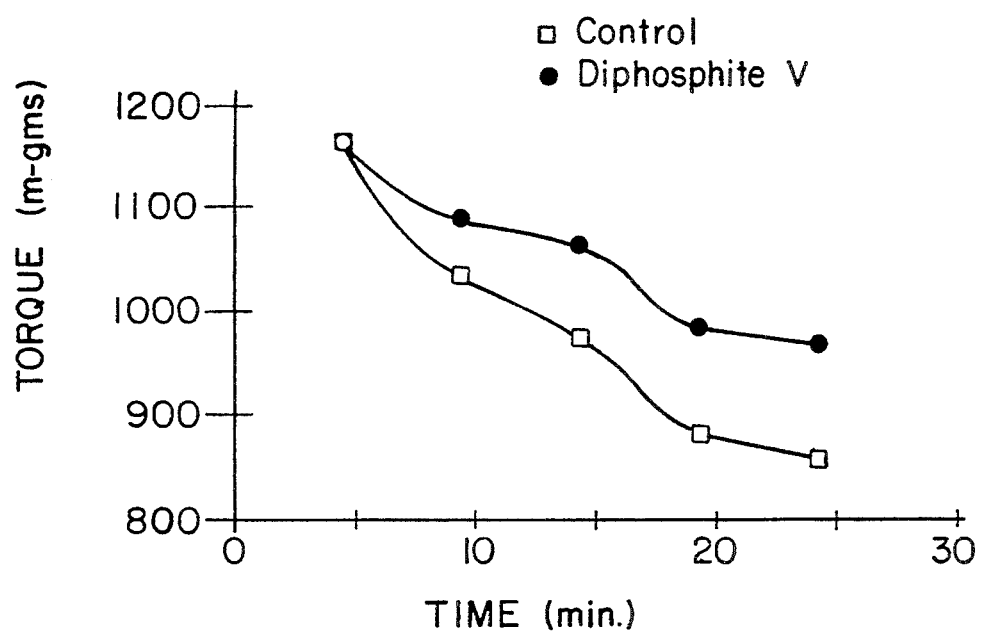
FIG. 5 is a plot of Torque (meter grams) vs. time (minutes) of the addition of 0.2% of the diphosphite described as (E) in FIG. 1 to polycarbonate.
Figure 6:
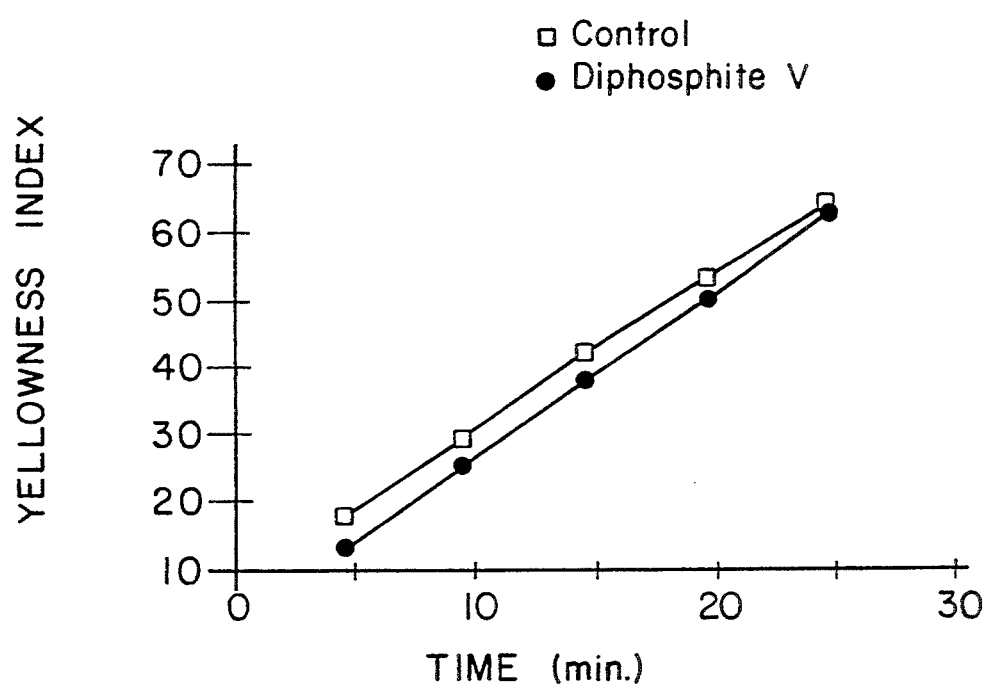
FIG. 6 is a plot of Yellow Index vs. time (minutes) using the same comparatives shown for FIG. 5.

FIG. 5 shows that the addition of 0.2% of the bis(2,4-dicumylphenyl)pentaerythritol diphosphite of formula (V) to Lexan 15 1 branched polycarbonate results in a significant improvement in melt stability as shown by the Torque Rheometer data. The test was run for 25 minutes at 300° C. and 100 rpm.

Similarly, the color stability of the polycarbonate was also improved with the addition of the diphosphite additive as shown in FIG. 5 wherein the Yellowness Index was also measured on samples taken from the Torque Rheometer run above.

EXAMPLES

The best mode for carrying out the invention will now be described for the purposes of illustrating the best mode known to the applicant at the time. The examples are illustrative only and not meant to limit the invention, as measured by the scope and spirit of the claims.

Example #1

Preparation of bis(2,4-dicumylphenyl)pentaerythritol diphosphite of formula (V)

A glass reactor was fitted with an agitator, reflux condenser, and a gas outlet. The reactor was charged with 150 g of 2,4-dicumylphenol, 100 g heptane and 100 g toluene and heated to 35° C. After sufficient mixing, 62.6 g of PCl3 were added and the reaction mixture heated to 90° C. After 0.5 hours at 90°-95° C., HCl was still evolving. The reaction is allowed to proceed for approximately 1.25 hours at 90°-95° C., followed by cooling to 45° C. with the addition of 31.4 g of pentaerythritol under vigorous agitation. The reaction is allowed to proceed with agitation for about 3 hours at 50° C. A nitrogen purge was initiated over the reaction and 120 g of additional heptane was added to the batch with heating to 100° C. for 8 hours. The product is a milky-white suspension. After cooling, filtering and drying, 129 g of bis(2,4-dicumylphenyl)pentaerythritol diphosphite was recovered (66% yield). The acid number varied from 2 to 6. The mother liquor can be recycled into another batch to produce additional product if desired.

Example #2

Preparation of bis(2,4-dicumylphenyl)pentaerythritol diphosphite of formula (V)with added trialkanolamine A glass reactor was fitted with an agitator, reflux condenser, and a gas outlet. The reactor was charged with 150 g of 2,4-dicumylphenol, 0.22 g of triethanolamine, 100 g heptane and 100 g toluene and heated to 35° C. After sufficient mixing, 62.6 g of PCl3 were added and the reaction mixture heated to 90° C. After 0.5 hours at 90°–95° C., HCl was still evolving. The reaction is allowed to proceed for approximately 1.25 hours at 90°–95° C., followed by cooling to 45° C. with the addition of 31.4 g of pentaerythritol under vigorous agitation. The reaction is allowed to proceed with agitation for about 3 hours at 50° C. A nitrogen purge was initiated over the reaction and 120 g of additional heptane was added to the batch with heating to 100° C. for 8 hours. The product is a milky-white suspension. After cooling, filtering and drying, 147 g of bis(2,4-dicumylphenyl)pentaerythritol diphosphite was recovered (75.4% yield). The acid number varied from 1 to 6, and generally from 1 to 3. The mother liquor can be recycled into another batch to produce additional product if desired.

The addition of a trialkanol amine increasing the yield of bis(2,4-dicumylphenyl)pentaerythritol diphosphite from 66% to more than 75% as shown by reaction Schematic I.

C. or less as well as 2 additional grams of sodium metal for the transesterification reaction. The reaction temperature was held at 175° C. for approximately 12 hours under nitrogen atmosphere. By-product phenol was then distilled from the reaction solution at 200°–2 10° C. under 3 to 5 mm vacuum. After cooling the reaction temperature to 175° C., 2,500 g of xylene (dry) were added and the product crystallized through the addition of 2,500 g of isopropanol (dry) at 60° C. After cooling the product to room temperature, the crystallized product was solvent washed with isopropanol several times and dried under vacuum at 70° C. The melting point of the bis(2,4-dicumylphenyl)pentaerythritol diphosphite of formula (V) was 230°–232° C. with an acid number of less than 1. The product appearance was white to off-white free-flowing powder, of 98%+purity by differential scanning calorimetry.

In this synthetic procedure, 2,4-dicumylphenol is used as a solvent and can be added from 0 to 100% molar excess. In a preferred embodiment, the molar

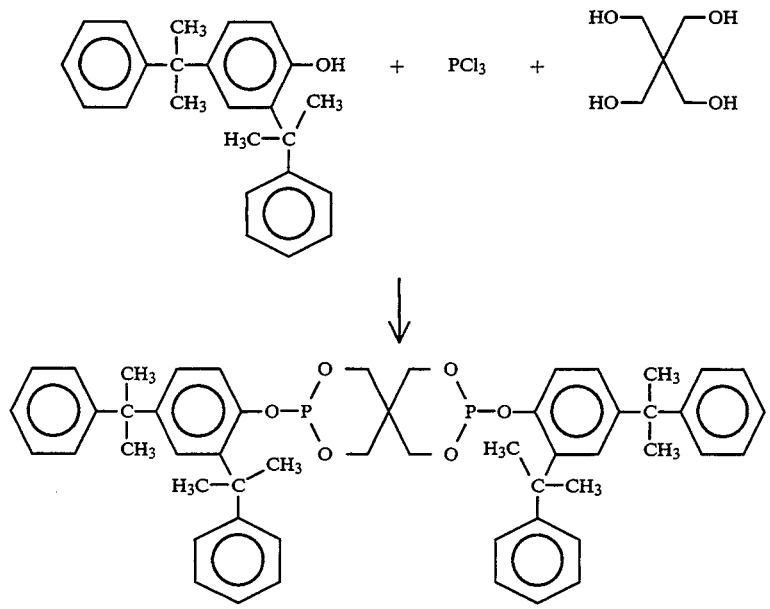

Schematic I

Example #3
Preparation of bis(2,4-dicumylphenyl)pentaerythritol diphosphite of formula (V)

Dry triphenylphosphite (2,582 g) were charged into a reactor at room temperature under a nitrogen atmosphere. Pentaerythritol (mono) (566 g) were added while slowly stirring the solution, as was ;phenol (40 g) After the addition, 1 g of sodium metal were added to the reactor solution, with the evolution of hydrogen gas. The batch was slowly heated to 120 to 125° C. and held at that temperature for 5 hours, followed by subsequent cooling to 100° C. By-product phenol was distilled off at 3-4 mm vacuum at 125°–130° C. 2,4-Dicumylphenol (dry, 95%+purity) was added at 125° excess is approximately 50%. The intermediate diphenyl pentaerythritol diphosphite is prepared initially using sodium metal as a catalyst, but other alkali catalysts are also expected to be useful in the reaction. The reaction temperature is generally carried out between 175°–200° C. followed by the distillation of phenol, which is recovered. After the phenol is distilled off, the batch is cooled to 175° C. and xylene added. The batch is further cooled to approximately 60° C. and ispropanol added to precipitate the product which is then filtered and dried. The product, with an acid number of less than 1, has a high spiral content, anywhere from 90%, to more typically greater than 98% as determined by phosphorus NMR.

Schematic II

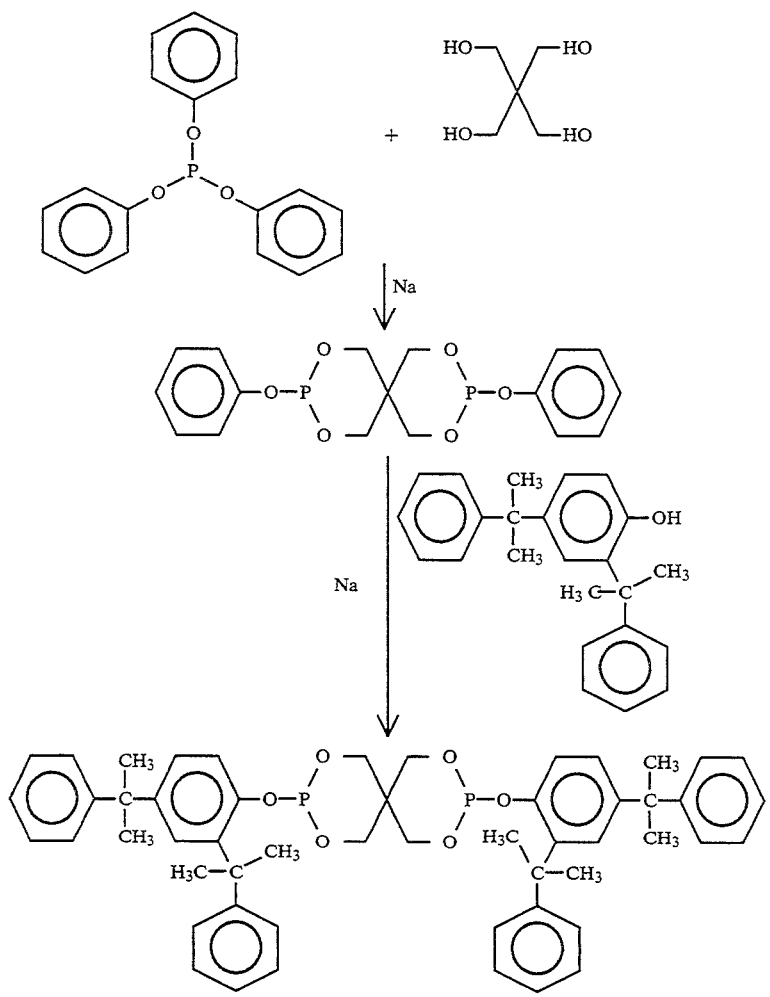

In general, the synthetic procedures used to prepare the bis(2,4-dicumylphenyl)pentaerythritol diphosphite of formula (V) are shown in Schematics I and II. It is of course recognized that while only one specific embodiment is shown, others would be possible. For example, the benzene rings could contain alkyl, typically of $C_{1-4}$ and/or halogen, typically chlorine and bromine, substituents, and still be within the spirit of the invention. Additionally, the reaction times, temperatures and use of other solvents have not been maximized, the specific examples being the best known to the inventors as of the date of the application.

DISCUSSION

While the present invention has been directed to just a few stabilized polymer compositions which are primarily polyolefins, polycarbonates, polyesters, etc., there is no need to limit it to such. In fact, any of the polymers known in the art, such as polyesters, polyurethanes, polyalkylene terephthalates, polysulfones, polyimides, polyphenylene ethers, styrenic polymers, polycarbonates, acrylic polymers, polyamides, polyacetals, halide containing polymers and polyolefin homopolymers and copolymers. Additionally included would be mixtures of different polymers, such as polyphenylene ether/styrenic resin blends, polyvinylchloride/ABS or other impact modified polymers, such as methacrylonitrile containing ABS, and polyester/ABS or polyester plus some other impact modifier may also be used. Such polymers are available commercially or may be made by means well known in the art. However, the diphosphites of the invention are particularly useful in thermoplastic polymers, such as polyolefins, polycarbonates, polyesters, polyphenylene ethers and styrenic polymers, due to the extreme temperatures at which the thermoplastic polymers are often processed and/or used.

Polymers of monoolefins and diolefins, for example would include polypropylene, polyisobutylene, polybutene-1, polymethylpentene-1, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE) and linear low density polyethylene (LLDPE) may be used. Mixtures of these polymers, for example mixtures of polypropylene with polyisobutylene, polypropylene with polyethylene (for example PP/HDPE), may also be used. Also useful are copolymers of monoolefins and diolefins with each other or with other vinyl monomers, such as, for example, ethylene/propylene, LLDPE and its mixtures with LDPE, propylene/butene-1, ethylene/hexene, ethylene/ethylpentene, ethylene/heptene, ethylene/octene, propylene/butadiene, isobutylene/isoprene, ethylene/alkyl acrylates, ethylene/alkyl methacrylates, ethylene/vinyl acetate (EVA) or ethylene/acrylic acid copolymers (EAA) and their salts (ionomers) and terpolymers of ethylene with propylene and a diene, such as hexadiene, dicyclopentadiene or ethylidene-norbornene; as well as mixtures of such copolymers and their mixtures with polymers mentioned above, for example polypropylene/ethylene-propylene copolymers, LDPE/EVA, LDPE/EAA, LLDPE/EVA and LLDPE/EAA.

Thermoplastic polymers may also include styrenic polymers, such as polystyrene, poly-(p-methylstyrene), poly-(α-methylstyrene), copolymers of styrene or α-methylstyrene with dienes or acrylic derivatives, such as, for example, styrene/butadiene, styrene/acrylonitrile, styrene/alkyl methacrylate, styrene/maleic anhydride, styrene/budadiene/ethyl acrylate, styrene/acrylonitrile/methacrylate; mixtures of high impact strength from styrene copolymers and another polymer, such as, for example, from a polyacrylate, a diene polymer or an ethylene/propylene/diene terpolymer; and block copolymers of styrene, such as, for example, styrene/butadiene/styrene, styrene/isoprene/styrene, styrene/ethylene/butylene/styrene or styrene/ethylene/propylene/styrene. Styrenic polymers may additionally or alternatively include graft copolymers of styrene or α-methylstyrene such as, for example, styrene on polybutadiene, styrene on polybutadiene-styrene or polybutadiene-acrylonitrile; styrene and acrylonitrile (or methacrylonitrile) on polybutadiene; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures of with the styrenic copolymers indicated above.

Nitrile polymers are also useful in the polymer composition of the invention. These include homopolymers and copolymers of acrylonitrile and its analogs such as methacrylonitrile, such as polyacrylonitrile, acrylonitrile/butadiene polymers, acrylonitrile/alkyl acrylate polymers, acrylonitrile/alkyl methacrylate/butadiene polymers, acrylonitrile/butadiene/styrene (ABS), and ABS which includes methacrylonitrile.

Polymers based on acrylic acids, such as acrylic acid, methacrylic acid, methyl methacrylate acid and ethacrylic acid and esters thereof may also be used. Such polymers include polymethylmethacrylate, and ABS-type graft copolymers wherein all or part of the acrylonitrile-type monomer has been replaced by an acrylic acid ester or an acrylic acid amide. Polymers including other acrylic-type monomers, such as acrolein, methacrolein, acrylamide and methacrylamide may also be used.

Halogen-containing polymers may also be useful. These include resins such as polychloroprene, epichlorohydrin homopolymers and copolymers, polyvinyl chloride, polyvinyl bromide, polyvinyl fluoride, polyvinylidene chloride, chlorinated polyethylene, chlorinated polypropylene, fluorinated polyvinylidene, brominated polyethylene, chlorinated rubber, vinyl chloride-vinylacetate copolymer, vinyl chloride-ethylene copolymer, vinyl chloride-propylene copolymer, vinyl chloride-styrene copolymer, vinyl chloride-isobutylene copolymer, vinyl chloride-vinylidene chloride copolymer, vinyl chloride-styrene-maleic anhydride tercopolymer, vinyl chloride-styrene-acrylonitrile copolymer, vinyl chloride-isoprene copolymer, vinyl chloride-chlorinated propylene copolymer, vinyl chloride-vinylidene chloride-vinyl acetate tercopolymer, vinyl chloride-acrylic acid ester copolymers, vinyl chloride-maleic acid ester copolymers, vinyl chloride-methacrylic acid ester copolymers, vinyl chloride-acrylonitrile copolymer and internally plasticized polyvinyl chloride.

Other useful thermoplastic polymers include homopolymers and copolymers of cyclic ethers, such as polyalkylene glycols, polyethylene oxide, polypropylene oxide or copolymers thereof with bis-glycidyl ethers; polyacetals, such as polyoxymethylene and those polyoxymethylene with contain ethylene oxide as a comonomer; polyacetals modified with thermoplastic polyurethanes, acrylates or methacrylonitrile containing ABS; polyphenylene oxides and sulfides, and mixtures of polyphenylene oxides with polystyrene or polyamides; polycarbonates and polyester-carbonates; polysulfones, polyethersulfones and polyetherketones; and polyesters which are derived from dicarboxylic acid and diols and/or from hydroxycarboxylic acids or the corresponding lactones, such as polyethylene terephthalate, polybutylene terephthalate, poly-1,4-dimethyliol-cyclohexane terephthalate, poly-[2,2,4-(4-hydroxyphenyl)-propane]terephthalate and polyhydroxybenzoates as well as block copolyetheresters derived from polyethers having hydroxyl end groups.

Polyamides and copolyamides which are derived from diamines and dicarboxylic acids and/or from aminocarboxylic acids or the corresponding lactams, such as polyamide-4, polyamide-6, polyamide-6/6, polyamide-6/10, polyamide-6/9, polyamide-6/12, polyamide-4/6, polyamide- 11, polyamide- 12, aromatic polyamides obtained by condensation of m-xylene, diamine and adipic acid; polyamides prepared from hexamethylene diamine and isophthalic and/or terephthalic acid and optionally an elastomer as modifier, for example, poly-2,4,4-trimethylhexamethylene terephthalamide or poly-m-phenylene isophthalamide may be useful. Further copolymers of the aforementioned polyamides with polyolefins, olefin copolymers, ionomers or chemically bonded or grafted elastomers; or with polyethers, such as for instance, with polyethylene glycol, polypropylene glycol or polytetramethylene glycols, and polyamides or copolyamides modified with EPDM or ABS may be used.

The resulting stabilized polymer compositions of the invention may optionally also contain various conventional additives, such as the following:

(1) Antioxidants (1.1) Alkylated monophenols, for example: 2,6-di-t-butyl-4-methylphenol, 2-t-butyl-4,6-dimethylphenol, 2,6-di-t-butyl-4-ethylphenol, 2,6-di-t-butyl-4-n-butylphenol, 2,6-di-t-butyl-4-butylphenol, 2,6-di-cyclopentyl-4-methylphenol, 2(α-methylcyclohexyl)-4,6-dimethylphenol, 2,6-di-octadecyl-4-methylphenol, 2,4,6-tricyclohexylphenol, and 2,6-di-t-butyl-4-methoxymethylphenol.

(1.2) Alkylated hydroquinones, for example, 2,6-di-t-butyl-4-methoxyphenol, 2,5-di-t-butyl-hydroquinone, 2,5-di-t-amyl-hydroquinone, and 2,6-diphenyl-4-octadecyloxyphenol.

(1.3) Hydroxylated thiodiphenyl ethers, for example, 2,2'-thio-bis-(6-t-butyl-4-methylphenol), 2,2'-thio-bis-(4- octylphenol), 4,4'-thio-bis-(6-t-butyl-3-methylphenol), and 4,4'-thio-bis-(6-t-butyl-2-methylphenol).

(1.4) Alkylidene-bisphenols, for example, 2,2'-methylene-bis-(6-t-butyl-4-methylphenol), 2,2'-methylene-bis-(6-t-butyl-4-ethylphenol), 2,2'-methylene-bis-[4-methyl-6-(alpha-methylcyclohexyl)phenol], 2,2'-methylene-bis-(4-methyl-6-cyclohexylphenol), 2,2'-methylene-bis-(6-nonyl-4-methylphenol), 2,2'-methylene-bis-[6-(α-methylbenzyl)-4-nonylphenol], 2,2'-methylene-bis-[6-(α,α-dimethylbenzyl)-4-nonylphenol], 2,2'-methylene-bis-(4,6-di-t-butylphenol), 2,2'-ethylidene-bis-(4,6-di-t-butylphenol), 4,4'-methylene-bis-(6-t-butyl-2-methylphenol), 1,1-bis-(5-t-butyl-4-hydroxy-2-methylphenyl)-butane, 2,6-di-(3-t-butyl-5-methyl-2-hydroxybenzyl)-4-methylphenol, 1,1,3-tris-( 5-t-butyl-4-hydroxy-2-methylphenyl)butane, 1,1-bis-(5-t-butyl-4-hydroxy-2-methylphenyl)-3-dodecylmercaptobutane, ethylenglycol-bis-[3,3-bis-(3 '-t-butyl-4'-hydroxy-phenyl)-butyrate], di-(3-t-butyl-4-hydroxy-5-methylphenyl)-dicyclopentadiene, and di-[2-(3'-t-butyl-2'-hydroxy-5'-methyl-benzyl)-6-t-butyl-4-methylphenyl]terephthalate.

(1.5) Benzyl compounds, for example, 1,3,5-tris-(3,5-di-t-butyl-4-hydroxybenzyl)-2,4,6-trimethylbenzene, bis(3,5-di-t-butyl-4-hydroxybenzyl)sulfide, isooctyl-3,5-di-t-butyl-4-hydroxybenzyl-mercapto-acetate, bis-(4-t-butyl-3-hydroxy-2,6-dimethylbenzyl)dithiolterephthalate, 1,3,5-tris-( 3,5-di-t-butyl-4-hydroxybenzyl)isocyanurate, 1,3,5-tris(4-t-butyl-3-hydroxy-2,6-dimethylbenzyl)isocyanurate, dioctadecyl-3,5-di-t-butyl-4-hydroxybenzyl-phosphonate, calcium salt of monoethyl 3,5-di-t-butyl-4-hydroxybenzylphosphonate, and 1,3,5-tris-1,3,5-dicyclohexyl-4-hydroxybenzyl)isocyanurate.

(1.6) Acylaminophenols, for example, 4-hydroxy-lauric acid anilide, 4-hydroxy-stearic acid anilide, 2,4-bis-octylmercapto-6-(3,5-t-butyl-4-hydroxy-anilino)-s-triazine, and octyl-N-(3,5-di-t-butyl-4-hydroxyphenyl)-carbamate.

(1.7) Esters of β-(3,5-di-t-butyl-4-hydroxyphenyl)-propionic acid with monohydric or polyhydric alcohols, for example, methanol, diethyleneglycol, octadecanol, triethyleneglycol, 1,6-hexanediol, pentaerythritol, neopentylglycol, tris-hydroxyethyl isocyanurate, thiodiethyleneglycol, and dihydroxyethyl oxalic acid diamide.

(1.8) Esters of β-(5-t-butyl-4-hydroxy-3-methylphenyl)-propionic acid with monohydric or polyhydric alcohols, for example, methanol, diethyleneglycol, octadecanol, triethyleneglycol, 1,6-hexanediol, pentaerythritol, neopentyglycol, tris-hydroxyethyl isocyanurate, thiodiethyleneglycol, and di-hydroxyethyl oxalic acid diamide.

(1.9) Esters of β-(5-t-butyl-4-hydroxy-3-methylphenyl)propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl)isocyanurate, thiodiethylene glycol, and N,N'-bis(hydroxyethyl)oxalic acid diamide.

(1.10) Amides of β-(3,5-di-t-butyl-4-hydroxyphenyl)-propionic acid, for example, N,N'-di-(3,5-di-t-butyl-4-hydroxyphenylpropionyl)-hexamethylendiamine, N,N'-di-(3,5-di-t-butyl-4-hydroxyphenylpropionyl)-trimethylendiamine, and N,N'-di-(3,5-di-t-butyl-4-hydroxyphenylpropionyl)-hydrazine.

(2) UV absorbers and light stabilizers.

(2.1) 2-(2'-Hydroxyphenyl)-benzotriazoles, for example, the 5 '-methyl-, 3',5'-di-t-butyl-, 5'-t-butyl-, 5'-(1,1,3,3-tetramethylbutyl)-, 5-chloro-3'-, 5'-di-t-butyl-, 5-chloro-3'-t-butyl-5'-methyl-, 3'-sec-butyl-5'-t-butyl-, 4'-octoxy, 3',5'-di-t-amyl-, and 3',5'-bis-(α,α-dimethylbenzyl) -derivatives.

(2.2) 2-Hydroxy-benzophenones, for example, the 4-hydroxy-, 4-methoxy-, -octoxy-, 4-decyloxy-, 4-dodecyloxy-, 4-benzyloxy-, 4,2',4'-trihydroxy- and 2'-hydroxy-4,4'-dimethoxy- derivatives.

(2.3) Esters of substituted and unsubstituted benzoic acids, for example, phenyl salicylate, 4-t-butyl-phenyl salicilate, octylphenyl salicylate, dibenzoyl-resorcinol, bis-(4-t-butylbenzoyl)-resorcinol, benzoylresorcinol, 2,4-di-t-butyl-phenyl-3,5-di-t-butyl-4-hydroxybenzoate and hexadecyl-3,5-di-t-butyl-4-hydroxybenzoate.

(2.4) Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, and N-(β-carbomethoxy-β-cyano-vinyl)-2-methyl-indoline.

(2.5) Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-di-ethanolamine, nickel dibutyl-dithiocarbamate, nickel salts of 4-hydroxy-3,5-di-t-butylbenzylphosphonic acid monoalkyl esters, such as of the methyl, ethyl or butyl ester, nickel complexes of ketoximes such as of 2-hydroxy-4-methyl-pentyl undecyl ketoxime, and nickel complexes of 1-phenyl-4-lauroyl-5-hydroxy-pyrazol, optionally with additional ligands.

(2.6) Sterically hindered amines, for example bis-(2,2,6,6-tetramethylpiperidyl)-sebacate, bis-(1,2,2,6,6-pentamethylpiperidyl)-sebacate, n-butyl-3,5-di-t-butyl-4-hydroxybenzyl malonic acid, bis-( 1,2,2,6,6-pentamethylpiperidyl)ester, condensation product of 1-hydroxyethyl-2,2,6,6-tetramethyl-4-hydroxy-piperidine and succinic acid, condensation product of N,N'-(2,2,6,6-tetramethylpiperidyl)-hexamethylendiamine and 4-t-octylamino-2,6-dichloro- 1,3,5-s-triazine, tris-(2,2,6,6-tetramethylpiperidyl)-nitrilotriacetate, tetrakis-(2,2,6,6-tetramethyl-4-piperidyl)- 1,2,3,4-butane-tetracarbonic acid, 1,1'-(1,2-ethanediyl)-bis-(3,3,5,5-tetramethyl-piperazinone). Such amines include hydroxylamines derived from hindered amines, such as di-(1-hydroxy-2,2,6,6-tetramethylpiperidin-4-yl)sebacate; 1-hydroxy-2,2,6,6-tetramethyl-4-benzoxypiperidine; 1-hydroxy-2,2,6,6-tetramethyl-4(3,5-di-t-butyl-4-hydroxyhydrocinnamoyloxy)piperidine; and N-(1-hydroxy-2,2,6,6-tetramethylpiperidin-4-yl)-ε-caprolactam.

(2.7) Oxalic acid diamides, for example, 4,4'-di-octyloxy-oxanilide, 2,2'-di-octyloxy-5,5-di-t-butyl-oxanilide, 2,2 '-di-dodecyloxy-5,5 '-di-t-butyl-oxanilide, 2-ethoxy-2 '-ethyl-oxanilide, N,N'-bis(3-dimethylaminopropyl)-oxalamide, 2-ethoxy-5-t-butyl-2 '-ethyloxanilide and its mixture with 2-ethoxy-2 '-ethyl-5,4'-di-t-butyloxanilide and mixtures of o-methoxy and p-methoxy as well as of o-ethoxy and p-ethoxy disubstituted oxanilides.

(3) Metal deactivators, for example, N,N'-diphenyloxalic acid diamide, N-salicylal-N'-salicyloylhydrazine, N,N'-bis-salicyloylhydrazine, N,N'-bis-(3,5-di-t-butyl-4-hydroxyphenylpropionyl)-hydrazine, salicyloylamino-1,2,4-triazole, bis-benzyliden-oxalic acid dihydrazide.

(4) Phosphites and phosphonites
for example triphenyl phosphite, diphenylalkyl phosphites, phenyldialkyl phosphites, tris(nonyl-phenyl)

phosphite, trilauryl phosphite, trioctadecyl phosphite, distearyl pentaerythritol diphosphite, tris(2,4-di-t-butylphenyl)phosphite, diisodecyl pentaeythritol diphosphite, bis(2,4-di-t-butylphenyl)pentaerythritol diphosphite, tristearyl sorbitol triphosphite, and tetrakis(2,4-di-t-butylphenyl) 4,4'-biphenylene diphosphonite.

(5) Peroxide scavengers for example esters of $\beta$-thiodipropionic acid, for example the lauryl, stearyl, myristyl or tridecyl esters, mercaptobenzimidazole or the zinc salt of 2-mercaptobenzimidazole, zinc-dibutyl-dithiocarbamate, dioctadecyldisulfide, pentaerythritol-tetrakis($\beta$-dodecylmercapto)-propionate.

(6) Polyamide stabilizers for example copper salts in combination with iodides and/or phosphorus compounds and salts of divalent manganese.

(7) Basic co-stabilizers for example, malamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, barium stearate, magnesium stearate, sodium ricinoleate, potassium palmirate, antimony pyrocatecholate and zinc pyrocatecholate.

Nucleating agents, for example, 4-t-butyl-benzoic acid, adipic acid, diphenylacetic acid.

(9) Fillers and reinforcing agents for example, calcium carbonate, silicates, glass fibers, asbestos, talc, kaolin, mica, barium sulfate, metal oxides and hydroxides, carbon black, graphite.

(10) Aminoxy propanoate derivatives such as methyl-3-[N,N-dibenzylaminoxy]propanoate; ethyl-3-[N,N-dibenzylaminoxy]propanoate; 1,6-hexamethylene-bis[3-(N,N-dibenzylaminoxy)propanoate]; methyl-[2-(methyl)-3(N,N-dibenzylaminoxy)propanoate]; octadecyl-3-[N,N-dibenzyl-aminoxy]propanoic acid; tetrakis[(N,N-dibenzylaminoxy)ethyl carbonyl oxymethyl]methane; octadecyl-3-[N,N-diethylaminoxy]propanoate; 3-[N,N-dibenzylaminoxy]propanoic acid potassium salt; and 1,6-hexamethylene bis[3-(N-allyl-N-dodecyl aminoxy)propanoate].

(11) Other additives for example, plasticizers, lubricants, emulsifiers, pigments, optical brighteners, flame-proofing agents, antistatic agents, blowing agents and thiosynergists such as dilaurylthiodipropionate or distearylthiodipropionate.

Hindered phenolic antioxidants may also be present in the polymer composition. Use of bis-aralkylphenyl pentaerythritol diphosphites of the present invention may result in enhanced polymer protection by reducing the formation of color resulting from the presence of the phenols. Such phenolic antioxidants include in addition to those specifically mentioned previously, n-octadecyl-3,5-di-t-butyl-4-hydroxyhydrocinnamate, neopentanterayl tetrakis-(3,5-di-t-butyl-4-hydroxylhydrocinnamate), di-n-octadecyl-3,5-di-t-butyl-4-hydroxybenzyl-phosphonate, 1,3,5-tris(3,5-di-t-butyl-4-hydroxybenzyl-)isocyanurate, thiodiethylene-bis(3,5-di-t-butyl-4-hydroxyhydrocinnamate), 1,3,5-trimethyl-2,4,6-tris(3,5-di-t-butyl-4-hydroxybenzyl)benzene, 3,6-di-oxaoctamethylene bis(3-methyl-5-t-butyl-4-hydroxyhydrocinnamate), 2,6-di-t-butyl-p-cresol, 2,2'-ethylidene-bis(4,6-di-t-butylphenol), 1,3,5-tris-(2,6-di-methyl-4-t-butyl-3-hydroxybenzyl)isocyanurate, 1,1,3-tris-(2-methyl-4-hydroxy-5-t-butylphenyl)butane, 1,3,5-tris[2-(3,5-di-t-butyl-4-hydroxyhydrocinnamoloxy)-ethyl]-isocyanurate, 3,5-di-(3,5-di-t-butyl-4-hydroxybenzyl)-mesitol, hexamethylene-bis(3,5-di-t-butyl-4-hydroxyhydrocinnamate), 1-(3,5-di-t-butyl-4-hydroxyanilino)-3,5-di(octylthio)-s-triazine, N,N'-hexamethylene-bis(3,5-di-t-butyl-4-hydroxyhydro-cinnamamide), calcium bis-(ethyl-3,5-di-t-butyl-4-hydroxybenzylphosphonate), ethylene bis[3,3-di(3-t-butyl-4-hydroxyphenyl)butyrate], octyl 3,5-di-t-butyl-4-hydroxybenzylmercaptoacetate, bis(3,5-di-t-butyl-4-hydroxyhydrocinnamoyl)-hydrazide, and N,N'-bis-[2-(3,5-t-butyl-4-hydroxyhydroxocinnamoyloxy)-ethyl]-oxamide, and preferably neopentanetetrayltetrakis(3,5-di-t-butyl-4-hydroxyhydrocinnamate), n-octadecyl-3,5-di-t-butyl-4-hydroxyhydrocinnamate, 1,3,5-trimethyl-2,4,6-tris(3,5-di-t-butyl-4-hydroxy-benzyl)benzene, 1,3,5-tris-(3,5-di-t-butyl-4-hydroxybenzyl)isocyanurate, 2,6-di-t-butyl-p-cresol or 2,2'-ethylidene-bis(4,6-di-t-butylphenol).

Other additives, such as oxazaphospholidines, may additionally or alternatively be present. Likewise, the instant compounds prevent color formation when hindered amine light stabilizers are present, such hindered amines including bis(1,2,2,6,6-pentamethyl-4-piperidyl)-2-n-butyl-2-(3,5-di-t-butyl-4-hydroxy-benzyl) malonate; bis(2,2,6,6-tetramethyl-4-piperidyl) sebacate; dimethylsuccinate polymer with 4-hydroxy-2,2,6,6-tetramethyl-1-piperidinethanol; and polymers of 2,4-dichloro-6-octylamino-s-triazine with N'-(2,2,6,6-tetramethyl-4-piperidyl)hexamethylene diamine.

Consistent with the invention, the bis-aralkylphenyl pentaerythritol diphosphites of the invention or the product of the process of the invention may be added to the polymer at any time prior to or during fabrication into articles, and may be combined with the polymer by any of a variety of means known in the art, such as by preblending or by being fed directly into fabrication equipment.

The invention has been described with reference to preferred and alternate embodiments. Obviously, modifications and alterations will occur to others upon the reading and understanding of the specification. It is intended to include all such modifications and alterations insofar as they come within the scope of the appended claims or the equivalents thereof.

What is claimed is:

1. A diphosphite of formula (IV) with improved resistance to hydrolysis and increased thermal stability comprising:

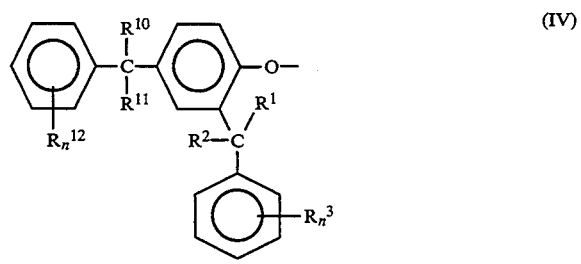

(IV)

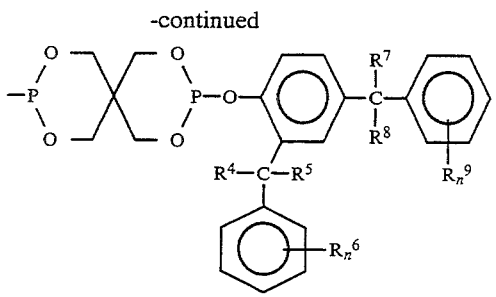

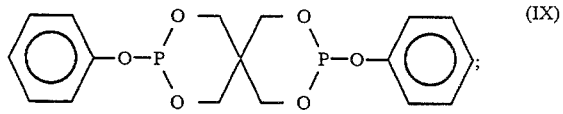

and wherein $R^1$, $R^2$, $R^4$, $R^5$, $R^7$, $R^8$, $R^{10}$ and $R^{11}$ are selected independently from the group consisting of hydrogen and alkyl radicals of generic formula $C_mH_{2m+1}$ wherein m ranges from 1 to 4 and $R^3$, $R^6$, $R^9$ and $R^{12}$ are selected independently from the group consisting of hydrogen, halogens and alkyl radicals of generic formula $C_mH_{2m+1}$ wherein m ranges from 1 to 4, and further wherein n ranges from to 3.

2. The composition of claim 1 with improved resistance to hydrolysis, as measured by having an acid number of 6.13 or less after exposure to 85% relative humidity at 25° C. for 163 hours.

3. A process for the preparation of a diphosphite of formula (IV)

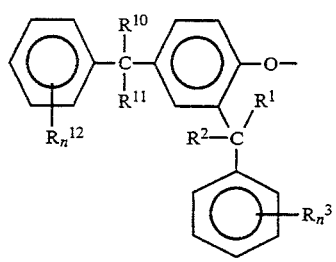

(IV)

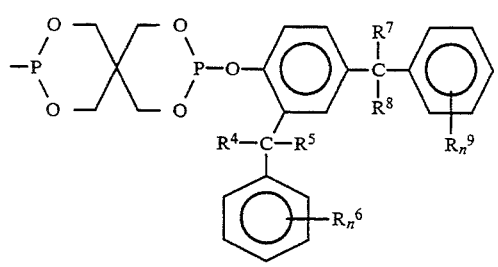

and wherein $R^1$, $R^2$, $R^4$, $R^5$, $R^7$, $R^8$, $R^{10}$ and $R^{11}$ are selected independently from the group consisting of hydrogen and alkyl radicals of generic formula $C_mH_{2m+1}$ wherein m ranges from 1 to 4 and $R^3$, $R^6$, $R^9$ and $R^{12}$ are selected independently from the group consisting of hydrogen, halogens and alkyl radicals of generic formula $C_mH_{2m+1}$ wherein m ranges from 1 to 4, and further wherein n ranges from to 3, comprising the steps of:

(a) adding at least one triaryl phosphite to pentaerythritol in the presence of an alkali metal catalyst to form a pentaerythritol diphosphite of formula (IX)

(IX)

(b) adding at least one aralkylphenol of formula (VI) and one aralkyl phenol of formula (VII) wherein formulas (VI) and (VII) may be the same or different in the presence of an alkali metal catalyst effecting the transesterification reaction,

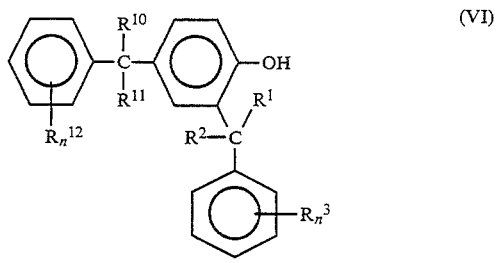

(VI)

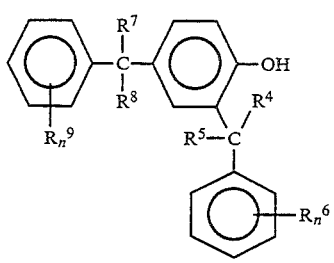

(VII)

to form the diphosphite of formula (IV).

4. The process of claim 3 which further comprises the step of heating to a temperature of between 175° C. to 200° C.

5. The process of claim 4 wherein the 2,4-dicumylphenol is both a solvent and a reactant and is added from 0 to 100% molar excess.

6. The process of claim 4 wherein the diphosphite is precipitated by the addition of an alcohol.

7. The process of claim 4 wherein the 2,4-dicumylphenol is added at 50% molar excess.

8. The diphosphite of claim 4 wherein the acid number is less than 1 after synthesis and the diphosphite has a spiral content greater than or equal to 90%.

9. The diphosphite of claim 4 wherein the spiral content is greater than or equal to 98%.

10. The process of claim 6 wherein the triarylphosphite is triphenylphosphite and the aralkylphenol is 2,4-dicumylphenol.

11. The composition of claim 8 which further comprises a polymer selected from the group consisting of polyolefin, polyester, polycarbonate, polyphenylene ether, and styrenic resins and mixtures thereof.

12. The composition of claim 7 wherein the polymer is selected from the group consisting of polyamide 6, polyamide 6/6, 6/10, 6/9, 6/12 and 4/6, polyethylene, polypropylene, polyethylene terephthalate, polybutylene terephthalate, polyphenylene ether, polycarbonate, polystyrene, impact polystyrene, ABS-type graft copolymer resins and mixtures thereof.

13. The composition of claim 12 wherein the diphosphite is present in an amount equal to about 0.1 to about 2 phr.

14. The composition of claim 13 wherein the diphosphite is present in an amount equal to about 0.1 to about 1 phr.

* * * * *